United States Patent
Moinet et al.

(10) Patent No.: US 9,150,529 B2
(45) Date of Patent: Oct. 6, 2015

(54) PIPERAZINE DERIVATIVES, METHODS FOR PREPARING SAME, AND USES THEREOF IN THE TREATMENT OF INSULIN RESISTANCE

(75) Inventors: Gerard Moinet, Orsay (FR); Gabriel Baverel, Saint Cyr au Mont D'or (FR); Remi Nazaret, Bourg En Bresse (FR); Bernard Ferrier, Lyon (FR)

(73) Assignee: METABOLYS (FR)

( * ) Notice: Subject to any disclaimer, the term of this patent is extended or adjusted under 35 U.S.C. 154(b) by 0 days.

(21) Appl. No.: 14/128,416

(22) PCT Filed: Jun. 22, 2012

(86) PCT No.: PCT/EP2012/062154
§ 371 (c)(1),
(2), (4) Date: Feb. 10, 2014

(87) PCT Pub. No.: WO2012/175715
PCT Pub. Date: Dec. 27, 2012

(65) Prior Publication Data
US 2014/0235650 A1    Aug. 21, 2014

(30) Foreign Application Priority Data
Jun. 23, 2011 (FR) ..................................... 11 55547

(51) Int. Cl.
| | | |
|---|---|---|
| C07D 241/04 | (2006.01) | |
| C07D 295/182 | (2006.01) | |
| C07D 295/192 | (2006.01) | |
| C07D 295/205 | (2006.01) | |
| C07D 295/26 | (2006.01) | |
| A61K 31/495 | (2006.01) | |
| A61K 31/496 | (2006.01) | |
| A61K 31/497 | (2006.01) | |
| C07D 295/092 | (2006.01) | |
| C07D 213/74 | (2006.01) | |
| C07D 241/20 | (2006.01) | |
| C07D 277/42 | (2006.01) | |
| C07D 295/088 | (2006.01) | |
| C07D 295/096 | (2006.01) | |
| C07D 295/155 | (2006.01) | |
| C07D 307/33 | (2006.01) | |
| C07D 495/04 | (2006.01) | |
| A61K 31/519 | (2006.01) | |
| A61K 45/06 | (2006.01) | |

(52) U.S. Cl.
CPC .......... *C07D 295/092* (2013.01); *A61K 31/495* (2013.01); *A61K 31/496* (2013.01); *A61K 31/497* (2013.01); *A61K 31/519* (2013.01); *A61K 45/06* (2013.01); *C07D 213/74* (2013.01); *C07D 241/04* (2013.01); *C07D 241/20* (2013.01); *C07D 277/42* (2013.01); *C07D 295/088* (2013.01); *C07D 295/096* (2013.01); *C07D 295/155* (2013.01); *C07D 295/182* (2013.01); *C07D 295/192* (2013.01); *C07D 295/205* (2013.01); *C07D 295/26* (2013.01); *C07D 307/33* (2013.01); *C07D 495/04* (2013.01)

(58) Field of Classification Search
CPC ............. C07D 241/04; C07D 295/182; C07D 295/192; C07D 295/205; C07D 295/26; A61K 31/495; A61K 31/496; A61K 31/497
See application file for complete search history.

(56) References Cited

U.S. PATENT DOCUMENTS

| | | | |
|---|---|---|---|
| 6,376,495 | B1 | 4/2002 | Moinet et al. |
| 7,012,071 | B2 | 3/2006 | Sharma et al. |
| 7,915,429 | B2 | 3/2011 | Sharma et al. |

FOREIGN PATENT DOCUMENTS

| | | |
|---|---|---|
| CN | 1558897 A | 12/2004 |
| CN | 101374414 A | 2/2009 |
| FR | 2781797 A1 | 2/2000 |
| WO | 0006558 A1 | 2/2000 |
| WO | 02100341 A2 | 12/2002 |

OTHER PUBLICATIONS

Agarwal, et al., Synthesis and pharmacological activities of 1-(2,4-disubstituted phenoxy)-3-[N1-(N4-arylpiperazinyl)]propanes and 1-(4-chlorobenzoyl)-3-substituted 6-methoxy-2-{4-[3-N1-(N4-phenylpiperazinyl)propoxy]phenyl}indoles, Indian Journal of Chemistry, Section B: Organic Chemistry Including Medicinal Chemistry, 30B(4), 413-16 (1991).*
Chinese Office Action dated Sep. 29, 2014 for Application No. 201280040455.5.
European Search Report dated Aug. 23, 2012 for Application No. PCT/EP2012/062154.
Bansal, Ranju, et al.; "Synthesis and Vasodilatory Activity of Some Amide Derivatives of 6-(4-caroxymethyloxyphenyl)-4,5-dihydro-3(2H)-pyridazinone"; European Journal of Medicinal Chemistry; vol. 44; pg. 4441-4447; 2009.

* cited by examiner

*Primary Examiner* — Erich A Lesser
(74) *Attorney, Agent, or Firm* — Cantor Colburn LLP

(57) ABSTRACT

The invention relates to a compound of formula (I), where $R^1$, $R^2$, $R^7$, m, n, and $L^1$ are as defined in claim 1, and to the methods for preparing same, to the pharmaceutical compositions containing same, and to the uses thereof in the treatment of diseases associated with insulin resistance syndrome.

(I)

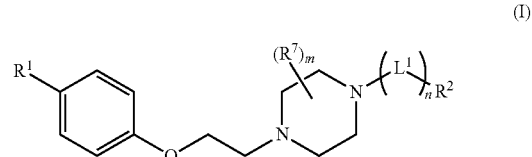

16 Claims, No Drawings

PIPERAZINE DERIVATIVES, METHODS FOR PREPARING SAME, AND USES THEREOF IN THE TREATMENT OF INSULIN RESISTANCE

CROSS REFERENCE TO RELATED APPLICATIONS

This application is filed in accordance with 35 U.S.C. §371 and claims benefit of PCT Patent Application Serial No. PCT/EP2012/062154, filed Jun. 22, 2012, and French Patent Application Serial No. 11 55547, filed Jun. 23, 2011, both of which are incorporated herein in their entirety.

The present invention concerns novel compounds useful in particular in the treatment of pathologies associated with the insulin resistance syndrome (or syndrome X), in particular in the treatment of type 2 diabetes.

A significant increase in the cases of diabetes in the world has been observed for a few years. Currently there are approximately 250 million diabetics in the world and the predictions for 2030 are around more than 400 million diabetics. Type 1 diabetes (destruction of the cells producing insulin) is mainly treated by the injection of insulin. Type 2 diabetes, which is more widespread (90% of diabetes cases), is characterised by a resistance of the tissues towards insulin and requires special treatment.

Numerous compounds have been proposed for treating diabetes, in particular type 2 diabetes. Piperazine derivatives are known in particular from EP 2781797. Phenylated derivatives are also known from WO 02/100341.

Currently, in approximately 40% of cases, the treatment is not effective and the required glycaemia threshold on an empty stomach of 1.2 g/liter of blood is not achieved.

It is therefore necessary to propose novel compounds affording more effective treatment of the pathologies associated with the insulin resistance syndrome.

One objective of the present invention is therefore to provide compounds effective in the treatment of the pathologies associated with the insulin resistance syndrome.

Another objective of the present invention is to provide a method for preparing these compounds.

Yet another objective of the present invention is to provide a means of treating pathologies associated with the insulin resistance syndrome, in particular type 2 diabetes. One objective of the present invention is to propose compounds in particular for inhibiting neoglucogenesis.

Yet other objectives will emerge from a reading of the following description of the invention.

The present invention concerns a compound of formula (I)

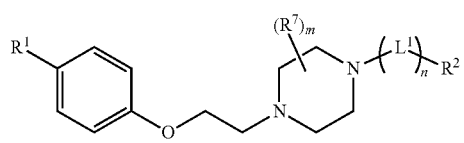

in which n represents 0 or 1, enantiomers, diastereoisomers thereof and the addition salts thereof with pharmaceutically acceptable bases or acids.

The present invention also relates to compound of formula (I) in which n=0, corresponding to compound of formula (Ia), enantiomers, diastereoisomers thereof and the addition salts thereof with pharmaceutically acceptable bases or acids

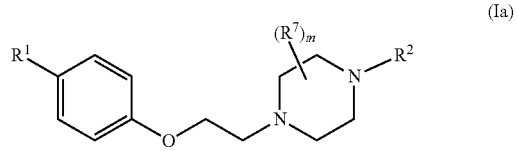

The present invention also relates to compound of formula (I) in which n=1, corresponding to compound of formula (Ib), enantiomers, diastereoisomers thereof and the addition salts thereof with pharmaceutically acceptable bases or acids

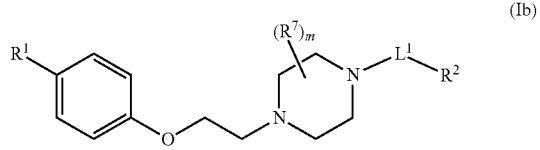

In the compounds of formula (I), (Ia) and (Ib) according to the invention:

$R^1$ represents:
  a —$C(O)CR^3R^4CR^5R^6C(O)OH$ group;
  a —$C(OH)(H)CR^3R^4CR^5R^6C(O)OH$ group; or
  a group

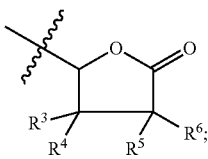

n represents 0 or 1;
m represents an integer ranging from 0 to 8;
$L^1$ represents a —C(O)—; —C(O)O— or —$S(O)_2$— group;
$R^2$ represents:
  a carbocycle group with 5, 6 or 7 members, saturated, partially unsaturated or aromatic, substituted or non-substituted;
  a polycarbocycle group with 8 to 14 members, preferably 9 or 10 members, saturated, partially unsaturated or aromatic, substituted or non-substituted;
  a heterocycle group with 5, 6 or 7 members, substituted or non-substituted, saturated, partially unsaturated or aromatic, which may comprise 1, 2 or 3 heteroatoms, identical or different, in particular chosen from nitrogen, oxygen or sulphur;
  a polyheterocycle group with 8 to 14 members, preferably 9 or 10 members, substituted or non-substituted, saturated, partially unsaturated or aromatic, which may comprise 1, 2 or 3 heteroatoms, identical or different, in particular chosen from nitrogen, oxygen or sulphur;
  a -$L^2$-carbocycle group, the carbocycle being in 5, 6 or 7 members, saturated, partially unsaturated or aromatic, substituted or non-substituted;
  a -$L^2$-polycarbocycle group, the polycarbocycle being in 8 to 14 members, preferably 9 or 10 members, saturated, partially unsaturated or aromatic, substituted or non-substituted;

a -$L^2$-heterocycle group, the heterocycle being in 5, 6 or 7 members, substituted or non-substituted, saturated, partially unsaturated or aromatic and which may comprise 1, 2 or 3 heteroatoms, identical or different, in particular chosen from nitrogen, oxygen or sulphur;

a -$L^2$-polyheterocycle group, the polyheterocycle being in 8 to 14 members, preferably 9 or 10 members, substituted or non-substituted, saturated, partially unsaturated or aromatic and which may comprise 1, 2 or 3 heteroatoms, identical or different, in particular chosen from nitrogen, oxygen or sulphur; or a hydrocarbon group, linear or branched, $C_1$ to $C_5$, preferably $C_1$ to $C_4$, preferably alkyl, linear or branched, $C_1$ to $C_5$, preferably $C_1$ to $C_4$;

$L^2$ being an alkyl, linear or branched, $C_1$ to $C_5$, preferably $C_1$ to $C_4$;

$R^3$, $R^4$, $R^5$ and $R^6$, identical or different, represent:
  a hydrogen atom;
  an alkyl group, linear or branched, $C_1$ to $C_5$, preferably $C_1$ to $C_4$;
  a carbocycle group with 5, 6 or 7 members, saturated, partially unsaturated or aromatic, substituted or non-substituted; or
  $R_3$ and $R_4$ form together with the carbon atom to which they are bonded a carbocycle with 5, 6 or 7 members, substituted or non-substituted, preferably saturated; for example cyclopentyl or cyclohexyl; or
  $R_5$ and $R_6$ form together with the carbon atom to which they are bonded a carbocycle with 5, 6 or 7 members, substituted or non-substituted, preferably saturated; for example cyclopentyl or cyclohexyl;

$R^7$, identical or different, represent:
  an alkyl, linear or branched, $C_1$ to $C_5$, preferably $C_1$ to $C_4$; for example methyl, ethyl, propyl, isopropyl, butyl, tert-butyl;
  a -$L^2$-carbocycle group, the carbocycle being in 5, 6 or 7 members, saturated, partially unsaturated or aromatic, substituted or non-substituted;
  a -$L^2$-polycarbocycle, the polycarbocycle being in 8 to 14 members, preferably 9 or 10 members, saturated, partially unsaturated or aromatic, substituted or non-substituted;
  a -$L^2$-heterocycle group, the heterocycle being in 5, 6 or 7 members, substituted or non-substituted, saturated, partially unsaturated or aromatic and which may comprise 1, 2 or 3 heteroatoms, identical or different, in particular chosen from nitrogen, oxygen or sulphur; or
  a -$L^2$-polyheterocycle group, the polyheterocycle being in 8 to 14 members, preferably 9 or 10 members, substituted or non-substituted, saturated, partially unsaturated or aromatic and which may comprise 1, 2 or 3 heteroatoms, identical or different, in particular chosen from nitrogen, oxygen or sulphur.

The carbocycles, polycarbocycles, heterocycles and polyheterocycles are non-substituted or substituted by one or more substituents, identical or different, in particular chosen from:
  a $C_1$ to $C_6$ alkoxy group, linear or branched, for example methoxy, ethoxy, propoxy, isopropoxy, butoxy or tert-butoxy;
  a halogen atom;
  a hydrocarbon group, linear or branched, preferably alkyl, $C_1$ to $C_5$, preferably $C_1$ to $C_4$, for example methyl, ethyl, propyl, butyl, isopropyl, tert-butyl;
  a hydrocarbon group, linear or branched, preferably alkyl, $C_1$ to $C_5$, preferably $C_1$ to $C_4$, substituted in particular by one or more halogen atoms;
  a cyano (—CN) group; or
  a sulfonylalkyl (—$S(O)_2$-alkyl) group, in which the alkyl is linear or branched, $C_1$ to $C_5$, preferably $C_1$ to $C_4$, for example methyl, ethyl, propyl, butyl, isopropyl or tert-butyl;
  a carbocycle group with 5, 6 or 7 members, saturated, partially unsaturated or aromatic, preferably phenyl, substituted or non-substituted, in particular by one or more substituents, identical or different, in particular chosen from a halogen atom, a $C_1$ to $C_6$ alkoxy group, linear or branched, for example methoxy, ethoxy, propoxy, isopropoxy, butoxy or tert-butoxy; an alkyl group, $C_1$ to $C_5$, preferably $C_1$ to $C_4$, for example methyl, ethyl, propyl, butyl, isopropyl or tert-butyl.

Preferably, in the compound of formula (I), (Ia) and (Ib), $R^1$ represents a —$C(O)CR^3R^4CR^5R^6C(O)OH$ group.

Preferably, in the compound of formula (I), (Ia) and (Ib), $R^7$, identical or different, represent:
  an alkyl, linear or branched, $C_1$ to $C_3$; or
  a -$L^2$-carbocycle group, $L^2$ being an alkyl, linear or branched, $C_1$ to $C_5$, preferably $C_1$ to $C_4$; and the carbocycle being aromatic with 5 or 6 members, for example phenyl, optionally substituted.

Preferably, in the compound of formula (I), (Ia) and (Ib) m represents 0 or 1, preferably 0.

Preferably, in the compound of formula (I), (Ia) and (Ib), $R^2$ represents:
  a carbocycle group with 6 members, non-substituted or substituted by one or more substituents, identical or different, in particular chosen from:
    a $C_1$ to $C_6$ alkoxy group, preferably $C_1$ to $C_3$, linear or branched, for example methoxy, ethoxy, propoxy, isopropoxy, butoxy or tert-butoxy;
    a halogen atom, for example fluorine, chlorine or bromine;
    a $C_1$ to $C_5$ alkyl group, preferably $C_1$ to $C_4$, linear or branched, for example methyl, ethyl, propyl, butyl, isopropyl or tert-butyl;
    a $C_1$ to $C_5$ alkyl group, preferably $C_1$ to $C_4$, linear or branched, substituted in particular by one or more halogen atoms, for example trifluoromethyl;
    a cyano (—CN) group; or
    a sulfonylalkyl (—$S(O)_2$-alkyl) group, in which the alkyl is linear or branched, $C_1$ to $C_5$, preferably $C_1$ to $C_4$, for example methyl, ethyl, propyl, butyl, isopropyl or tert-butyl, for example sulfonyl methane (—$S(O)_2CH_3$);
    an aryl group, preferably phenyl, substituted or non-substituted in particular by one or more substituents, identical or different, in particular chosen from a halogen atom, a $C_1$ to $C_6$ alkoxy group, linear or branched, for example methoxy, ethoxy, propoxy, isopropoxy, butoxy or tert-butoxy; a $C_1$ to $C_5$ alkyl group, preferably $C_1$ to $C_4$, for example methyl, ethyl, propyl, butyl, isopropyl or tert-butyl;
  a 5 or 6 member aromatic heterocycle group, comprising 1, 2 or 3 heteroatoms, identical or different, in particular chosen from nitrogen, sulphur and oxygen, non-substituted or substituted by one or more substituents, identical or different, in particular chosen from:
    a $C_1$ to $C_6$ alkoxy group, preferably $C_1$ to $C_3$, linear or branched, for example methoxy, ethoxy, propoxy, isopropoxy, butoxy or tert-butoxy;

a halogen atom, for example fluorine, chlorine or bromine;

a $C_1$ to $C_5$ alkyl group, preferably $C_1$ to $C_4$, linear or branched, for example methyl, ethyl, propyl, butyl, isopropyl or tert-butyl;

a $C_1$ to $C_5$ alkyl group, preferably $C_1$ to $C_4$, linear or branched, substituted in particular by one or more halogen atoms, for example trifluoromethyl;

a cyano (—CN) group; or a sulfonylalkyl (—S(O)$_2$-alkyl) group, in which the alkyl is linear or branched, $C_1$ to $C_5$, preferably $C_1$ to $C_4$, for example methyl, ethyl, propyl, butyl, isopropyl or tert-butyl, for example sulfonyl methane (—S(O)$_2$CH$_3$);

an aryl group, preferably phenyl, substituted or non-substituted in particular by one or more substituents, identical or different, in particular chosen from a halogen atom, a $C_1$ to $C_6$ alkoxy group, linear or branched, for example methoxy, ethoxy, propoxy, isopropoxy, butoxy or tert-butoxy; a $C_1$ to $C_5$ alkyl group, preferably $C_1$ to $C_4$, for example methyl, ethyl, propyl, butyl, isopropyl or tert-butyl;

the heterocycle is preferably non-substituted or substituted by a phenyl group, substituted or non-substituted in particular by one or more substituents, identical or different, in particular chosen from a halogen atom, a $C_1$ to $C_6$ alkoxy group, linear or branched, for example methoxy, ethoxy, propoxy, isopropoxy, butoxy or tert-butoxy; a $C_1$ to $C_5$ alkyl group, preferably $C_1$ to $C_4$, for example methyl, ethyl, propyl, butyl, isopropyl or tert-butyl;

an 8 to 14 member aromatic polyheterocycle, preferably 9 to 10 members, comprising 1, 2 or 3 heteroatoms, identical or different, chosen from nitrogen, sulphur and oxygen, non-substituted or substituted by one or more substituents, identical or different, in particular chosen from:

a $C_1$ to $C_6$ alkoxy group, preferably $C_1$ to $C_3$, linear or branched, for example methoxy, ethoxy, propoxy, isopropoxy, butoxy or tert-butoxy;

a halogen atom, for example fluorine, chlorine or bromine;

a $C_1$ to $C_5$ alkyl group, preferably $C_1$ to $C_4$, linear or branched, for example methyl, ethyl, propyl, butyl, isopropyl or tert-butyl;

a $C_1$ to $C_5$ alkyl group, preferably $C_1$ to $C_4$, linear or branched, substituted in particular by one or more halogen atoms, for example trifluoromethyl;

a cyano (—CN) group; or a sulfonylalkyl (—S(O)$_2$-alkyl) group, in which the alkyl is linear or branched, $C_1$ to $C_5$, preferably $C_1$ to $C_4$, for example methyl, ethyl, propyl, butyl, isopropyl or tert-butyl, for example sulfonyl methane (—S(O)$_2$CH$_3$);

an aryl group, preferably phenyl, substituted or non-substituted in particular by one or more substituents, identical or different, in particular chosen from a halogen atom, a $C_1$ to $C_6$ alkoxy group, linear or branched, for example methoxy, ethoxy, propoxy, isopropoxy, butoxy or tert-butoxy; a $C_1$ to $C_5$ alkyl group, preferably $C_1$ to $C_4$, for example methyl, ethyl, propyl, butyl, isopropyl or tert-butyl;

an alkyl group, linear or branched, $C_1$ to $C_5$, preferably $C_1$ to $C_4$, for example methyl, ethyl, propyl, butyl, isopropyl or tert-butyl; or a -$L^2$-carbocycle group, the carbocycle being aromatic with 5 or 6 members, for example phenyl, non-substituted or substituted by one or more substituents, identical or different, in particular chosen from:

a $C_1$ to $C_6$ alkoxy group, preferably $C_1$ to $C_3$, linear or branched, for example methoxy, ethoxy, propoxy, isopropoxy, butoxy or tert-butoxy;

a halogen atom, for example fluorine, chlorine or bromine;

a $C_1$ to $C_5$ alkyl group, preferably $C_1$ to $C_4$, linear or branched, for example methyl, ethyl, propyl, butyl, isopropyl or tert-butyl;

a $C_1$ to $C_5$ alkyl group, preferably $C_1$ to $C_4$, linear or branched, substituted in particular by one or more halogen atoms, for example trifluoromethyl;

a cyano (—CN) group; or a sulfonylalkyl (—S(O)$_2$-alkyl) group, in which the alkyl is linear or branched, $C_1$ to $C_5$, preferably $C_1$ to $C_4$, for example methyl, ethyl, propyl, butyl, isopropyl or tert-butyl, for example sulfonyl methane (—S(O)$_2$CH$_3$);

an aryl group, preferably phenyl, substituted or non-substituted in particular by one or more substituents, identical or different, in particular chosen from a halogen atom, a $C_1$ to $C_6$ alkoxy group, linear or branched, for example methoxy, ethoxy, propoxy, isopropoxy, butoxy or tert-butoxy; a $C_1$ to $C_5$ alkyl group, preferably $C_1$ to $C_4$, for example methyl, ethyl, propyl, butyl, isopropyl or tert-butyl;

$L^2$ being an alkyl group, linear or branched, $C_1$ to $C_5$, preferably $C_1$ to $C_4$, for example methyl, ethyl, propyl, butyl, isopropyl or tert-butyl.

Preferably, in the compound of formula (I), (Ia) and (Ib) $R^2$ represents:

a phenyl, non-substituted or substituted by one or more substituents, identical or different, in particular chosen from:

a $C_1$ to $C_6$ alkoxy group, preferably $C_1$ to $C_3$, linear or branched, for example methoxy, ethoxy, propoxy, isopropoxy, butoxy or tert-butoxy;

a halogen atom, for example fluorine, chlorine or bromine;

a $C_1$ to $C_5$ alkyl group, preferably $C_1$ to $C_4$, linear or branched, for example methyl, ethyl, propyl, butyl, isopropyl or tert-butyl;

a $C_1$ to $C_5$ alkyl group, preferably $C_1$ to $C_4$, linear or branched, substituted in particular by one or more halogen atoms, for example trifluoromethyl;

a cyano (—CN) group; or a sulfonylalkyl (—S(O)$_2$-alkyl) group, in which the alkyl is linear or branched, $C_1$ to $C_5$, preferably $C_1$ to $C_4$, for example methyl, ethyl, propyl, butyl, isopropyl or tert-butyl, for example sulfonyl methane (—S(O)$_2$CH$_3$);

a phenyl group, substituted or non-substituted in particular by one or more substituents, identical or different, in particular chosen from a halogen atom, a $C_1$ to $C_6$ alkoxy group, linear or branched, for example methoxy, ethoxy, propoxy, isopropoxy, butoxy or tert-butoxy; a $C_1$ to $C_5$ alkyl group, preferably $C_1$ to $C_4$, for example methyl, ethyl, propyl, butyl, isopropyl or tert-butyl; preferably the substituent or substituents are in ortho or para position on the phenyl;

a monocyclic or polycyclic heteroaryl chosen from

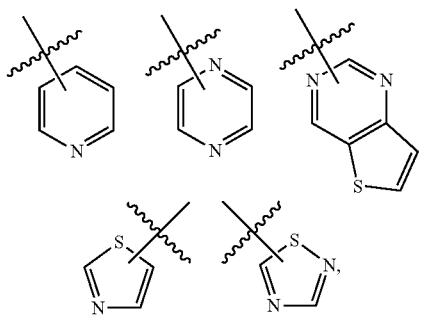

non-substituted or substituted by one or more substituents, identical or different, in particular chosen from:
- a $C_1$ to $C_6$ alkoxy group, preferably $C_1$ to $C_3$, linear or branched, for example methoxy, ethoxy, propoxy, isopropoxy, butoxy or tert-butoxy;
- a halogen atom, for example fluorine, chlorine or bromine;
- a $C_1$ to $C_5$ alkyl group, preferably $C_1$ to $C_4$, linear or branched, for example methyl, ethyl, propyl, butyl, isopropyl or tert-butyl;
- a $C_1$ to $C_5$ alkyl group, preferably $C_1$ to $C_4$, linear or branched, substituted in particular by one or more halogen atoms, for example trifluoromethyl;
- a cyano (—CN) group; or
- a sulfonylalkyl (—S(O)$_2$-alkyl) group, in which the alkyl is linear or branched, $C_1$ to $C_5$, preferably $C_1$ to $C_4$, for example methyl, ethyl, propyl, butyl, isopropyl or tert-butyl, for example sulfonyl methane (—S(O)$_2$CH$_3$);
- a phenyl group, substituted or non-substituted in particular by one or more substituents, identical or different, in particular chosen from a halogen atom, a $C_1$ to $C_6$ alkoxy group, linear or branched, for example methoxy, ethoxy, propoxy, isopropoxy, butoxy or tert-butoxy; a $C_1$ to $C_5$ alkyl group, preferably $C_1$ to $C_4$, for example methyl, ethyl, propyl, butyl, isopropyl or tert-butyl; preferably the mono or polycyclic heteroaryl is chosen from

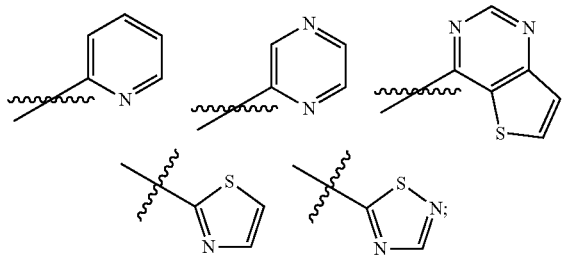

a -L$^2$-carbocycle group, the carbocycle being a phenyl, non-substituted or substituted by one or more substituents, identical or different, in particular chosen from:
- a $C_1$ to $C_6$ alkoxy group, preferably $C_1$ to $C_3$, linear or branched, for example methoxy, ethoxy, propoxy, isopropoxy, butoxy or tert-butoxy;
- a halogen atom, for example fluorine, chlorine or bromine;
- a $C_1$ to $C_5$ alkyl group, preferably $C_1$ to $C_4$, linear or branched, for example methyl, ethyl, propyl, butyl, isopropyl or tert-butyl;
- a $C_1$ to $C_5$ alkyl group, preferably $C_1$ to $C_4$, linear or branched, substituted in particular by one or more halogen atoms, for example trifluoromethyl;
- a cyano (—CN) group; or
- a sulfonylalkyl (—S(O)$_2$-alkyl) group, in which the alkyl is linear or branched, $C_1$ to $C_5$, preferably $C_1$ to $C_4$, for example methyl, ethyl, propyl, butyl, isopropyl or tert-butyl, for example sulfonyl methane (—S(O)$_2$CH$_3$);
- a phenyl group, substituted or non-substituted in particular by one or more substituents, identical or different, in particular chosen from a halogen atom, a $C_1$ to $C_6$ alkoxy group, linear or branched, for example methoxy, ethoxy, propoxy, isopropoxy, butoxy or tert-butoxy; a $C_1$ to $C_5$ alkyl group, preferably $C_1$ to $C_4$, for example methyl, ethyl, propyl, butyl, isopropyl or tert-butyl;

L$^2$ being an alkyl, linear or branched, $C_1$ to $C_5$, preferably $C_1$ to $C_4$, preferably methyl, ethyl, propyl, butyl, isopropyl, butyl or tert-butyl, for example —CH$_2$—; or
an alkyl group, linear or branched, $C_1$ to $C_5$, preferably $C_1$ to $C_4$, for example methyl, ethyl, propyl, butyl, isopropyl or tert-butyl.

Preferably, in the compound of formula (I), (Ia) and (Ib) R$^2$ represents:
- a phenyl, non-substituted or substituted by one or more substituents, identical or different, in particular chosen from:
  - a $C_1$ to $C_6$ alkoxy group, preferably $C_1$ to $C_3$, linear or branched, for example methoxy, ethoxy, propoxy, isopropoxy, butoxy or tert-butoxy;
  - a halogen atom, for example fluorine, chlorine or bromine;
  - a $C_1$ to $C_5$ alkyl group, preferably $C_1$ to $C_4$, linear or branched, for example methyl, ethyl, propyl, butyl, isopropyl or tert-butyl;
  - a $C_1$ to $C_5$ alkyl group, preferably $C_1$ to $C_4$, linear or branched, substituted in particular by one or more halogen atoms, for example trifluoromethyl;
  - a cyano (—CN) group; or
  - a sulfonylalkyl (—S(O)$_2$-alkyl) group, in which the alkyl is linear or branched, $C_1$ to $C_5$, preferably $C_1$ to $C_4$, for example methyl, ethyl, propyl, butyl, isopropyl or tert-butyl, for example sulfonyl methane (—S(O)$_2$CH$_3$);

preferably the substituent or substituents are in ortho or para position on the phenyl;
- a monocyclic or polycyclic heteroaryl chosen from

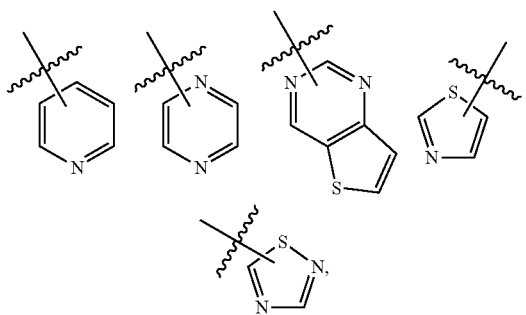

non-substituted or substituted by one or more substituents, identical or different, in particular chosen from:
- a $C_1$ to $C_6$ alkoxy group, preferably $C_1$ to $C_3$, linear or branched, for example methoxy, ethoxy, propoxy, isopropoxy, butoxy or tert-butoxy;
- a halogen atom, for example fluorine, chlorine or bromine;
- a $C_1$ to $C_5$ alkyl group, preferably $C_1$ to $C_4$, linear or branched, for example methyl, ethyl, propyl, butyl, isopropyl or tert-butyl;
- a $C_1$ to $C_5$ alkyl group, preferably $C_1$ to $C_4$, linear or branched, substituted in particular by one or more halogen atoms, for example trifluoromethyl;
- a cyano (—CN) group; or
- a sulfonylalkyl (—S(O)$_2$-alkyl) group, in which the alkyl is linear or branched, $C_1$ to $C_5$, preferably $C_1$ to $C_4$, for example methyl, ethyl, propyl, butyl, isopropyl or tert-butyl, for example sulfonyl methane (—S(O)$_2$CH$_3$);
- a phenyl group, substituted or non-substituted in particular by one or more substituents, identical or different, in particular chosen from a halogen atom, a $C_1$ to $C_6$ alkoxy group, linear or branched, for example methoxy, ethoxy, propoxy, isopropoxy, butoxy or tert-butoxy; a $C_1$ to $C_5$ alkyl group, preferably $C_1$ to $C_4$, for example methyl, ethyl, propyl, butyl, isopropyl or tert-butyl; preferably the mono or polycyclic heteroaryl is chosen from

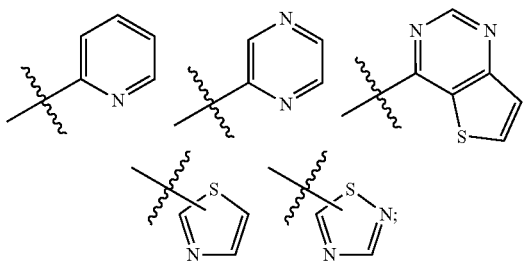

a -L$^2$-carbocycle group, the carbocycle being a phenyl, non-substituted or substituted by one or more substituents, identical or different, in particular chosen from:
- a $C_1$ to $C_6$ alkoxy group, preferably $C_1$ to $C_3$, linear or branched, for example methoxy, ethoxy, propoxy, isopropoxy, butoxy or tert-butoxy;
- a halogen atom, for example fluorine, chlorine or bromine;
- a $C_1$ to $C_5$ alkyl group, preferably $C_1$ to $C_4$, linear or branched, for example methyl, ethyl, propyl, butyl, isopropyl or tert-butyl;
- a $C_1$ to $C_5$ alkyl group, preferably $C_1$ to $C_4$, linear or branched, substituted in particular by one or more halogen atoms, for example trifluoromethyl;
- a cyano (—CN) group; or
- a sulfonylalkyl (—S(O)$_2$-alkyl) group, in which the alkyl is linear or branched, $C_1$ to $C_5$, preferably $C_1$ to $C_4$, for example methyl, ethyl, propyl, butyl, isopropyl or tert-butyl, for example sulfonyl methane (—S(O)$_2$CH$_3$);

L$^2$ being an alkyl, linear or branched, $C_1$ to $C_5$, preferably $C_1$ to $C_4$, preferably methyl, ethyl, propyl, butyl, isopropyl, butyl or tert-butyl, for example —CH$_2$—; or
an alkyl group, linear or branched, $C_1$ to $C_5$, preferably $C_1$ to $C_4$, for example methyl, ethyl, propyl, butyl, isopropyl or tert-butyl.

Preferably, in the compound of formula (I), (Ia) and (Ib), $R^3$, $R^4$, $R^5$ and $R^6$, identical or different, represent:
- a hydrogen atom;
- an alkyl group, linear or branched, $C_1$ to $C_5$, preferably $C_1$ to $C_4$, for example methyl, ethyl, propyl, butyl, isopropyl or tert-butyl;
- a carbocycle group with 5, 6 or 7 members, saturated, partially unsaturated or aromatic, preferably saturated, for example cyclopentyl or cyclohexyl, substituted or non-substituted; or
$R_3$ and $R_4$ form together with the carbon atom to which they are bonded a carbocycle with 5, 6 or 7 members, substituted or non-substituted, preferably saturated; for example cyclopentyl or cyclohexyl; or
$R_5$ and $R_6$ form together with the carbon atom to which they are bonded a carbocycle with 5, 6 or 7 members, substituted or non-substituted, preferably saturated; for example cyclopentyl or cyclohexyl.

Preferably, in the compound of formula (I), (Ia) and (Ib), $R^3$, $R^4$ each represents a hydrogen atom and $R^5$ and $R^6$, identical or different, represent:
- a hydrogen atom;
- an alkyl group, linear or branched, $C_1$ to $C_5$, preferably $C_1$ to $C_4$, for example methyl, ethyl, propyl, butyl, isopropyl or tert-butyl;
- a carbocycle group with 5, 6 or 7 members, saturated, partially unsaturated or aromatic, preferably saturated, for example cyclopentyl or cyclohexyl, substituted or non-substituted; or
$R_3$ and $R_4$ form together with the carbon atom to which they are bonded a carbocycle with 5, 6 or 7 members, substituted or non-substituted, preferably saturated; for example cyclopentyl or cyclohexyl; or
$R_5$ and $R_6$ form together with the carbon atom to which they are bonded a carbocycle with 5, 6 or 7 members, substituted or non-substituted, preferably saturated; for example cyclopentyl or cyclohexyl.

Preferably, in the compound of formula (I), (Ia) and (Ib), $R^3$, $R^4$, $R^5$ and $R^6$ each represents a hydrogen atom.

Polycarbocycle and polyheterocarbocycle according to the invention means carbocycles and polycyclic heterocarbocycles, in particular comprising two fused cycles.

Preferably, unless indicated to the contrary, in the compounds of formula (I), (Ia) and (Ib) according to the invention the polycarbocycles comprise 9 or 10 members and are substituted or non-substituted, preferably comprise 10 members, and are aromatic and substituted or non-substituted.

Preferably, and unless indicated to the contrary, in the compounds of formula (I), (Ia) and (Ib) according to the invention the polyheterocarbocycles comprise 9 or 10 members and may comprise 1, 2 or 3 heteroatoms, identical or different, in particular chosen from nitrogen, oxygen or sulphur, they are substituted or non-substituted, saturated, partially unsaturated or aromatic, preferably aromatic. The polyheterocarbocycles represent in particular

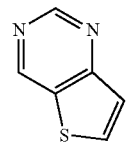

Preferably, and unless indicated to the contrary, in the compounds of formula (I), (Ia) and (Ib) according to the invention the carbocycles comprise 5 or 6 members, are saturated, partially unsaturated or aromatic, substituted or non-substituted, and preferably comprise 6 members and are aromatic, for example phenyl.

Preferably, and unless indicated to the contrary, in the compounds of formula (I), (Ia) and (Ib) according to the invention the heterocarbocycles comprise 5 or 6 members, and may comprise 1, 2 or 3 heteroatoms, identical or different, in particular chosen from nitrogen, oxygen or sulphur, they are substituted or non-substituted, saturated, partially unsaturated or aromatic, preferably aromatic. They are for example chosen from

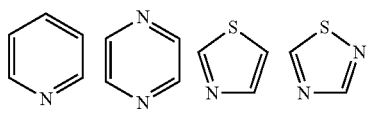

The invention also relates to the solvates of the compounds of formulae (I), (Ia) and (Ib).

The compounds of formulae (I), (Ia) and (Ib) have a carboxylic function and may be salified. They may then be in the form of addition salts with organic or mineral bases. The addition salts with bases are for example pharmaceutically acceptable salts such as sodium salts, potassium salts or calcium salts, which are obtained using corresponding alkaline-metal and alkaline-earth metal hydroxides as bases. As another type of addition salt with pharmaceutically acceptable bases, mention can be made of the salts with amines and in particular glucamine, N-methylglucamine, N,N-dimethylglucamine, ethanolamine, morpholine, N-methylmorpholine or lysine.

The compounds of formulae (I), (Ia) and (Ib) may also be salified with mineral or organic acids and preferably pharmaceutical acids such as hydrochloric, phosphoric, fumaric, citric, oxalic, sulphuric, ascorbic, tartric, maleic, mandelic, methanesulphonic, lactobionic, gluconic, glucaric, succinic, sulfonic or hydroxypropane sulfonic acids.

The present invention also concerns a first method (P1) for preparing compounds of formula (I), comprising:

(a) the protection of the acid function (carried by $R^1$) of a compound of formula (II)

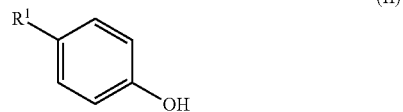

in which $R^1$ represents —C(O)CR$^3$R$^4$CR$^5$R$^6$C(O)OH;

(b) the reaction of the compound obtained at step (a) with a compound of formula $R^9$—(CH$_2$)$_2$—$R^8$ in which $R^8$ and $R^9$, identical or different, represent a leaving group, preferably $R^9$ is a better nucleofuge than $R^8$;

(c) the reaction of the compound obtained at step (c) with a compound of formula (III)

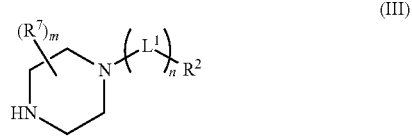

in which $L^1$, n, m, $R^2$ and $R^7$ have the definitions given by formula (I);

(d) deprotection of the compound obtained at step (c).

The starting products are commercial or can easily be prepared by a person skilled in the art on the basis of his general knowledge of organic chemistry.

The compounds for which $R^1$ represents —(OH)(H)CR$^3$R$^4$CR$^5$R$^6$C(O)OH can be obtained by reduction of the compounds for which $R^1$ represents —C(O)CR$^3$R$^4$CR$^5$R$^6$C(O)OH. This reduction may be carried out for example in the presence of NaBH$_4$ in ethanol. This reduction may, for example, occur between steps (b) and (c).

The compounds for which $R^1$ represents

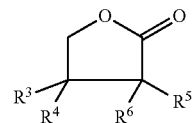

may be obtained by:
  lactonisation of the compounds for which $R^1$ represents —C(OH)(H)CR$^3$R$^4$CR$^5$R$^6$C(O)OH. This lactonisation will for example take place before step (c); or
  lactonisation of the compounds for which $R^1$ represents —C(O)CR$^3$R$^4$CR$^5$R$^6$C(O)OH. This lactonisation will for example take place after step (d).

These lactonisations may be carried out by any method known to persons skilled in the art and may for example be carried out in the presence of CF$_3$CO$_2$H in dichloromethane.

Step (a), corresponding to the protection of the acid function, may be performed in any manner known to persons skilled in the art, provided that the protection is selective of the acid function with respect to the alcohol function. Among the groups protecting the carboxylic function, those generally described in Protective Groups in Organic Synthesis, Greene T. W. and Wuts P. G. M, ed. John Wiley and Sons, 1991 and in Protective Groups, Kocienski P. J., 1994, Georg Thieme Verlag, may suit. By way of example the protection of the carboxylic function in the ester form (C$_1$-C$_6$ alkyl, for example methyl) can be envisaged. For example step (a) can be performed by reaction of the compound of formula (I) with methanol in the presence of an acid, in particular sulphuric acid.

Step (b) is preferably implemented in an aprotic polar solvent such as acetonitrile, dimethylformamide (DMF), acetone, dimethylsulfoxide and halogenated hydrocarbons such as dichloromethane or dichloroethane, at a suitable temperature, in particular between 15° and 80° C., preferably between 15° and 35° C. A preferred solvent is in particular acetonitrile. Advantageously, this step takes place in the presence of a base such as potassium carbonate. A person skilled in the art knows that a leaving group is all the more labile, the more stable the corresponding anionic species. Thus $R^9$ being more nucleofuge than $R^8$ corresponds to the fact that $R^{9-}$ is more stable than $R^{8-}$. The leaving groups $R^8$ and $R^9$, identical or different, are chosen from the halogen atoms, preferably chlorine and bromine; the (C$_6$-C$_{10}$)arylsulfonyloxy groups, the aryl group optionally being substituted by one or more C$_1$ to C$_6$ alkyl groups; the (C$_1$-C$_6$)alkylsulfonyloxy groups in which the alkyl group is optionally substituted by one or more halogen atoms. Preferably $R^8$ represents chlorine and $R^9$ represents bromine.

Step (c) is a nucleophile substitution step for which the operating conditions can easily be determined by a person skilled in the art. Advantageously, the reaction is implemented in an aprotic polar solvent in the presence of a base. Examples of suitable solvents are acetonitrile, dimethylformamide, acetone, dimethylsulfoxide and the halogenated hydrocarbons such as dichloromethane or dichloroethane. Alkaline or alkaline-earth metal carbonates, for example potassium carbonate, can be mentioned as a base. Advantageously, the reaction of step (c) is conducted at a temperature of 50° to 120° C., for example to reflux of the solvent in the presence of an alkaline metal iodide such as potassium iodide. The quantity of alkaline iodide may be variable and depends essentially on the nature of the reagents, the nature of the solvent and the reaction temperature. The reaction is generally stoichiometric. It is nevertheless possible to work with a slight excess of one or other of the reagents.

The deprotection step (d) may be any deprotection known to persons skilled in the art and compatible with the protection used at step (a) for recovering the acid function. For example, it may be a saponification in basic, acid or catalytic medium (Pd/C).

For preparing the compound of formula (Ia), the same method (P1) applies with the compound of formula (IIIa)

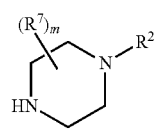

(IIIa)

in which m, $R^2$ and $R^7$ are as defined for formula (Ia).

The starting products are commercial or can easily be prepared by a person skilled in the art on the basis of his general knowledge of organic chemistry.

For preparing the compound of formula (Ib), the same method (P1) applies with the compound of formula (IIIb)

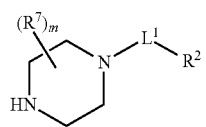

(IIIb)

in which $L^1$, n, m, $R^2$ and $R^7$ have the definitions given by formula (Ib).

The starting products are commercial or can easily be prepared by a person skilled in the art on the basis of his general knowledge of organic chemistry.

The invention also concerns a second method (P2) for preparing a compound of formula (I) comprising:
(i) the reaction of a compound of formula (III) with a compound of formula $R^9$—$(CH_2)_2$—$R^8$, in which $R^8$ and $R^9$ are as defined in the method (P1);
(ii) the protection of the acid function of a compound of formula (II);
(iii) the reaction between the compound obtained at step (i) and the compound obtained at step (ii);
(iv) the deprotection of the compound obtained at step (iii).

The starting products are commercial or can easily be prepared by a person skilled in the art on the basis of his general knowledge of organic chemistry.

The compounds for which $R^1$ represents —(OH)(H)CR$^3$R$^4$CR$^5$R$^6$C(O)OH can be obtained by reduction of the compounds for which $R^1$ represents —C(O)CR$^3$R$^4$CR$^5$R$^6$C(O)OH. This reduction may be carried out for example in the presence of NaBH$_4$ in ethanol. This reduction may, for example, occur between steps (ii) and (iii).

The compounds for which $R^1$ represents

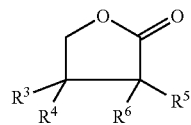

may be obtained by:
lactonisation of the compounds for which $R^1$ represents —C(OH)(H)CR$^3$R$^4$CR$^5$R$^6$C(O)OH. This lactonisation will for example take place before step (iii); or
lactonisation of the compounds for which $R^1$ represents —C(O)CR$^3$R$^4$CR$^5$R$^6$C(O)OH. This lactonisation will for example take place after step (iv).

These lactonisations may be carried out by any method known to persons skilled in the art and may for example be carried out in the presence of $CF_3CO_2H$ in dichloromethane.

There generally exists an equilibrium between the forms for which $R^1$ represents —C(OH)(H)CR$^3$R$^4$CR$^5$R$^6$C(O)OH and the forms for which $R^1$ represents

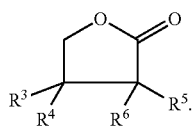

Step (i) is preferably implemented in an aprotic polar solvent such as acetonitrile, dimethylformamide (DMF), acetone, dimethylsulfoxide and halogenated hydrocarbons such as dichloromethane or dichloroethane, at a suitable temperature, in particular between 15° and 80° C., preferably between 15° and 35° C. A preferred solvent is in particular acetonitrile. Advantageously, this step takes place in the presence of a base such as potassium carbonate.

Step (ii), corresponding to the protection of the acid function, may be performed in any manner known to persons skilled in the art, provided that the protection is selective of the acid function with respect to the alcohol function. Among the groups protecting the carboxylic function, those generally described in Protective Groups in Organic Synthesis, Greene T. W. and Wuts P. G. M, ed. John Wiley and Sons, 1991 and in Protective Groups, Kocienski P. J., 1994, Georg Thieme Verlag, may suit. By way of example the protection of the carboxylic function in the ester form ($C_1$-$C_6$ alkyl, for example methyl) can be envisaged. For example step (a) can be performed by reaction of the compound of formula (I) with methanol in the presence of an acid, in particular sulphuric acid.

Step (iii) is a nucleophile substitution step for which the operating conditions can easily be determined by a person skilled in the art. Advantageously, the reaction is implemented in an aprotic polar solvent in the presence of a base. Examples of suitable solvents are acetonitrile, dimethylformamide, acetone, dimethylsulfoxide and the halogenated hydrocarbons such as dichloromethane or dichloroethane. Alkaline or alkaline-earth metal carbonates, for example potassium carbonate, can be mentioned as a base. Advantageously, the reaction of step (c) is conducted at a temperature of 50° to 120° C., for example to reflux of the solvent in the presence of an alkaline metal iodide such as potassium iodide. The quantity of alkaline iodide may be variable and depends essentially on the nature of the reagents, the nature of the solvent and the reaction temperature. The reaction is generally stoichiometric. It is nevertheless possible to work with a slight excess of one or other of the reagents.

The deprotection step (iv) may be any deprotection known to persons skilled in the art and compatible with the protection used at step (ii) for recovering the acid function. For example, it may be a saponification in basic, acid or catalytic medium (Pd/C).

For preparing the compound of formula (Ia), the same method (P2) applies with the compound of formula (IIIa)

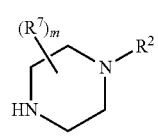

(IIIa)

in which m, $R^2$ and $R^7$ are as defined for formula (Ia).

The starting products are commercial or can easily be prepared by a person skilled in the art on the basis of his general knowledge of organic chemistry.

For preparing the compound of formula (Ib), the same method (P2) applies with the compound of formula (IIIb)

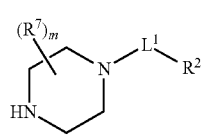

(IIIb)

in which $L^1$, n, m, $R^2$ and $R^7$ have the definitions given by formula (Ib).

The starting products are commercial or can easily be prepared by a person skilled in the art on the basis of his general knowledge of organic chemistry.

The compounds of the present invention are useful as medication. They are in particular useful for treating pathologies associated with the insulin-resistance syndrome (or syndrome X), in particular of type 2 diabetes.

The invention also concerns the use of the compounds according to the invention in combination with other treatments, in particular at least one other anti-diabetic agent, for example chosen from insulin, sulfonyl-urea (for example glibenclamide, glimepiride, glipizide), the thiazoline-diones, the glinides, the DPP-IV inhibitor (inhibitor of dipeptidylpeptidase), GLP-1 (Glucagon-like peptide-1) or analogues thereof.

Advantageously, the compounds of the invention have a strong activity of inhibiting neoglucogenesis.

Advantageously, the compounds of the invention exhibit a glucose consumption activity.

The invention also concerns the use of a compound according to the invention for preparing a medication.

The invention also concerns the use of a compound according to the invention for preparing a medication for treating pathologies associated with the insulin-resistance syndrome (or syndrome X), in particular type 2 diabetes.

The present invention also concerns pharmaceutical compositions comprising by way of active principle at least one compound according to the invention. These compositions may also comprise a pharmaceutically acceptable vehicle and/or excipient.

The pharmaceutical compositions may be in any forms known to persons skilled in the art, in particular in the forms intended for administration by parenteral, oral, rectal, permucosal or percutaneous method, preferably orally.

The compositions according to the invention will be presented in the form of injectable solutes or suspensions or multi-dose flasks, in the form of bare or coated tablets, pills, capsules, powders, suppositories or rectal capsules, solutions or suspensions, for percutaneous use, in a polar solvent, or permucosal use.

The excipients that are suitable for such administrations are derivatives of cellulose or microcrystalline cellulose, alkaline-earth carbonates, magnesium phosphate, starches, modified starches or lactose for solid forms.

For rectal use, cocoa butter or polyethylene glycol stearates are the preferred excipients.

For parenteral use, water, aqueous solutes, physiological serum and isotonic solutes are the vehicles most conveniently used.

The posology may vary within large limits according to the therapeutic indication and the administration method, as well as the age and weight of the subject.

The invention also concerns a composition comprising, by way of active principle, at least one compound according to the invention in combination with at least one other anti-diabetic agent, for example chosen from insulin, sulfonyl-urea (for example glibenclamide, glimepiride, glipizide), the thiazoline-diones, the glinides, the DPP-IV inhibitor (inhibitor of dipeptidylpeptidase), GLP-1 (Glucagon-like peptide-1) or analogues thereof.

These compositions also comprise a pharmaceutically acceptable vehicle or excipient.

The invention also concerns a method of treating pathologies associated with the insulin-resistance syndrome (or syndrome X), in particular type 2 diabetes, comprising the administration, to the patient who so requires, of a sufficient quantity of at least one compound according to the invention with a pharmaceutically acceptable vehicle or excipient.

The identification of the patient who needs the treatment indicated above is defined by a person skilled in the art. A veterinary or a doctor may identify, by means of clinical tests, physical examination, biological tests or diagnoses and by the family and/or medical history, the subjects who need such a treatment.

Sufficient quantity means a quantity of compound according to the present invention effective for preventing or treating pathological conditions. The sufficient quantity may be determined by a person skilled in the art, by means of conventional technology and by the observation of the results obtained in similar circumstances. To determine the sufficient quantity, various factors must be taken into account by a person skilled in the art, in particular and without being limited thereto: the subject, his size, his age, his general state of health, the illness involved and the degree of severity thereof; the response of the subject, the type of compound, the administration method, the bioavailability of the composition administered, the dosage, the concomitant use of other medications, etc. Preferably, 5 to 500 mg/day of the compound according to the invention is administered to the patient in one or more doses, preferably in one dose.

The present invention also concerns a method of treating pathologies associated with the insulin-resistance syndrome (or syndrome X), in particular type 2 diabetes, comprising the administration, to the patient who needs it, of a sufficient quantity of at least one compound according to the invention with a pharmaceutically acceptable vehicle or excipient and at least one other anti-diabetic agent, for example chosen from insulin, sulfonyl-urea (for example glibenclamide, glimepiride, glipizide), the thiazoline-diones, the glinides, the DPP-IV inhibitor (inhibitor of dipeptidylpeptidase), GLP-1 (Glucagon-like peptide-1) or analogues thereof.

The present invention will now be described with the help of non-limitative examples.

EXAMPLE 1

General Diagram for Preparing Compounds for which $R^1$ Represents $C(O)CR^3R^4CR^5R^6C(O)OH$

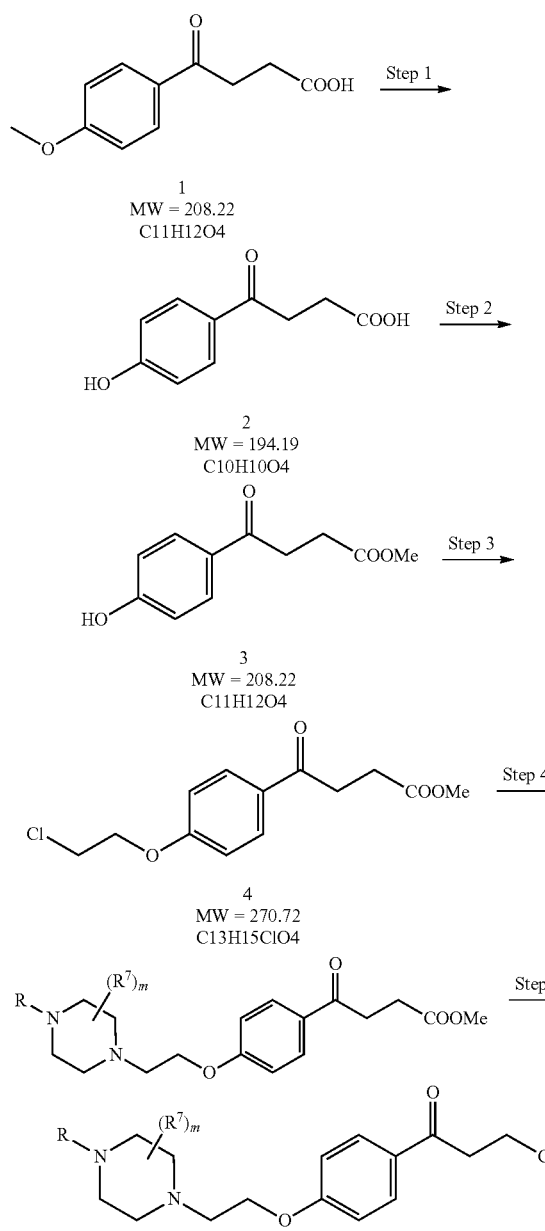

The first step is a demethylation step that can be performed by reaction of HBr in an acetic acid medium.

The second step is an esterification reaction that can be performed by reaction with methanol in the presence of sulphuric acid.

Steps 3 and 4 are nucleophilic substitution steps.

Step 5 can be performed in particular by acid hydrolysis or saponification.

Step 1: Demethylation

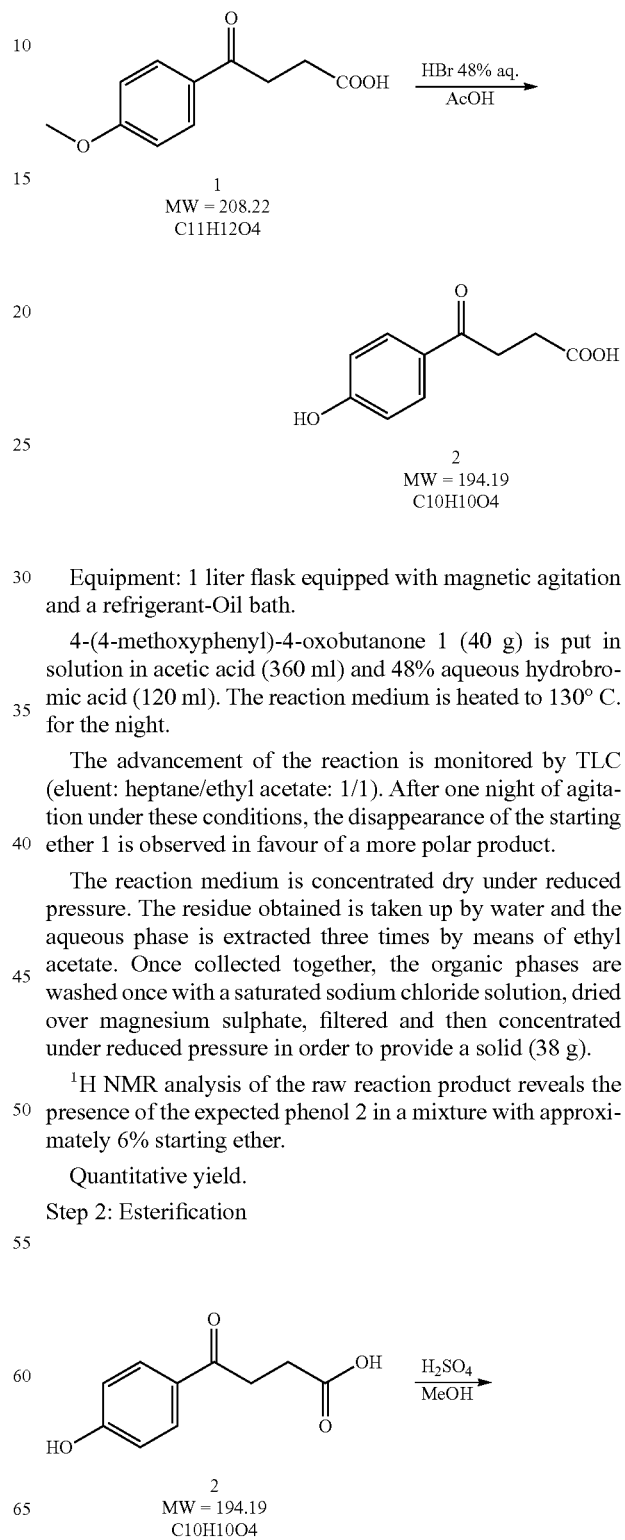

Equipment: 1 liter flask equipped with magnetic agitation and a refrigerant-Oil bath.

4-(4-methoxyphenyl)-4-oxobutanone 1 (40 g) is put in solution in acetic acid (360 ml) and 48% aqueous hydrobromic acid (120 ml). The reaction medium is heated to 130° C. for the night.

The advancement of the reaction is monitored by TLC (eluent: heptane/ethyl acetate: 1/1). After one night of agitation under these conditions, the disappearance of the starting ether 1 is observed in favour of a more polar product.

The reaction medium is concentrated dry under reduced pressure. The residue obtained is taken up by water and the aqueous phase is extracted three times by means of ethyl acetate. Once collected together, the organic phases are washed once with a saturated sodium chloride solution, dried over magnesium sulphate, filtered and then concentrated under reduced pressure in order to provide a solid (38 g).

$^1$H NMR analysis of the raw reaction product reveals the presence of the expected phenol 2 in a mixture with approximately 6% starting ether.

Quantitative yield.

Step 2: Esterification

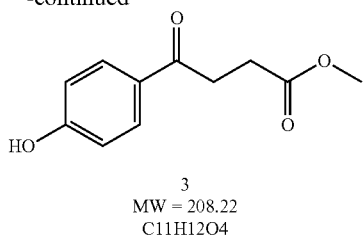

3
MW = 208.22
C11H12O4

Equipment: 1 liter three-necked flask equipped with magnetic agitation and a refrigerant and placed under nitrogen scavenging-Oil bath.

The 4-(4-hydroxyphenyl)-4-oxobutanoic acid derivative 2 (48 g) is put in solution in methanol (480 ml) before slowly pouring in sulphuric acid (48 ml). The solution thus obtained is heated at 70° C. for the night.

The advancement of the reaction is monitored by TLC (eluent: heptane/ethyl acetate: 1/1). After a night of agitation under these conditions, the disappearance of the starting acid 2 is observed in favour of a less polar product.

The reaction medium is concentrated dry under reduced pressure. The residue obtained is taken up by water (500 ml) and dichloromethane (500 ml). The heterogeneous medium is neutralised, carefully, with a saturated sodium hydrogenocarbonate solution (pH 7-8). The aqueous phase is then extracted three times with ethyl acetate. Once collected together, the organic phases are washed once with a saturated sodium chloride solution, dried on magnesium sulphate, filtered and then concentrated under reduced pressure in order to provide a solid (49.6 g).

$^1$H NMR analysis of the raw reaction medium reveals the presence of the expected ester 3 in a mixture with less than 3% of the methyl 4-(4-methoxyphenyl)-4-oxobutanoate compound.

Yield 96%.

Step 3: Nucleophilic Substitution

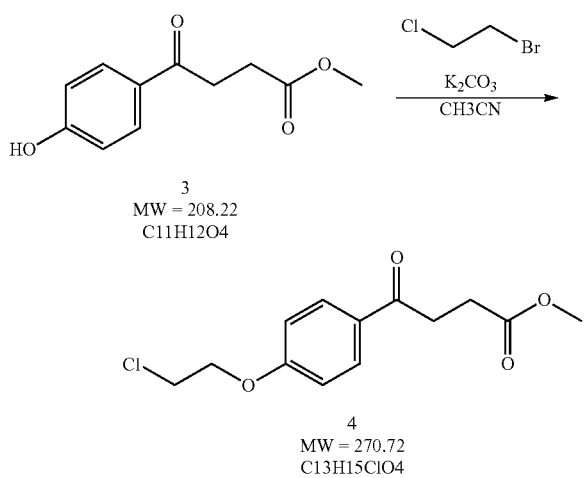

4
MW = 270.72
C13H15ClO4

Equipment: 1 liter 3-necked flask equipped with magnetic agitation and a refrigerant and placed under nitrogen scavenging-Oil bath.

The methyl 4-(4-hydroxyphenyl)-4-oxobutanoate 3 (49.6 g) is put in solution in acetonitrile (400 ml). Potassium carbonate (98.77 g) is added to the solution. The reaction medium is heated to 50° C. before pouring a solution of 1-bromo-2-chloroethane (102.5 g) into the acetonitrile (170 ml). The reaction medium is heated at 80° C. for the night.

The advancement of the reaction is monitored by TLC (eluent: heptane/ethyl acetate: 7/3). After 24 hours of agitation under these conditions, the disappearance of the compound 3 in favour of a less polar product is observed.

After return to ambient temperature, the reaction medium is filtered in order to eliminate the potassium carbonate. The potassium carbonate is rinsed with acetonitrile and then the filtrate is concentrated dry under reduced pressure. The residue obtained is taken up with water (500 ml) and the aqueous phase is extracted twice by means of ethyl acetate (600 ml). The organic phases are collected together, washed once with a 1 M sodium hydroxide solution (400 ml), dried on magnesium sulphate, filtered and then concentrated under reduced pressure in order to provide a beige solid (61.44 g).

$^1$H NMR analysis of the raw reaction product reveals the presence of the expected chlorinated derivative 4.

Yield 95%.

Step 4: Nucleophilic Substitution

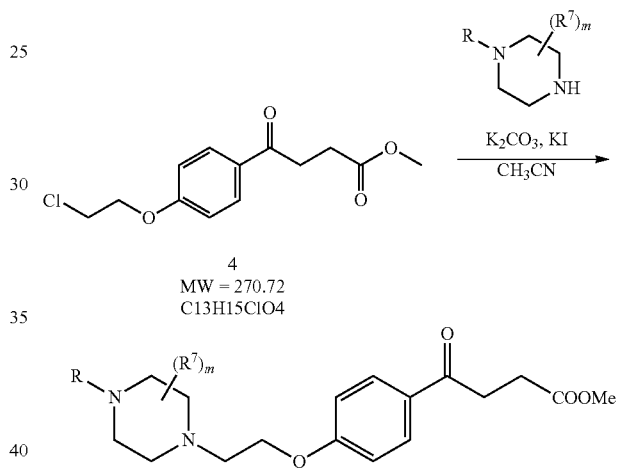

4
MW = 270.72
C13H15ClO4

Equipment: Stem apparatus equipped with a heating system and orbital agitation. 9 ml reactors-Manifold-Multivac evaporation system-Allexis extraction apparatus.

Under nitrogen scavenging, the chlorinated derivative 4 (500 mg, 1.85 mmol, 1 eq.) is distributed in the various reactors and then put in solution in acetonitrile (5 ml) in the presence of R-piperazine (1.85 mmol, 1 eq.), potassium carbonate (766 mg, 5.54 mmol, 3 eq.) previously dried, and potassium iodide (307 mg, 1.85 mmol, 1 eq.). After nitrogen scavenging has been carried out, the reactors are closed and heated to 80° C.

After 72 hours, the heating is stopped. After return to ambient temperature, the various reaction media are filtered in parallel on Supelco cartridge connected to a manifold in order to eliminate the inorganic salts. After rinsing with acetonitrile, the filtrates are concentrated dry under reduced pressure using the Multivac. The residues obtained are taken up with water (20 ml) and extracted three times, in parallel on Allexis apparatus, by means of ethyl acetate (10 ml). The various organic phases collected together are dried on magnesium sulphate, filtered and then concentrated under reduced pressure using the Multivac.

The various raw reaction substances are purified by chromatography on Redisep 40 g prepacked column, Biotage SP4 system, using a dichloromethane/methanol gradient.

Step 5: Acid Hydrolysis

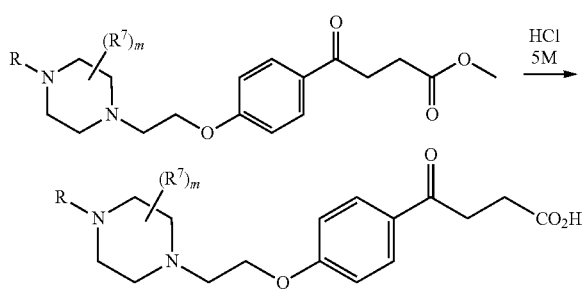

Equipment: Syncore-Heating system-orbital agitation-50 ml reactors

The various esters are put in solution in hydrochloric acid 5 and then the solutions are heated to 90° C. for 2 hours. Monitoring by TLC (Eluent: dichloromethane/methanol 98/2, UV revelation) of the reaction medium of each reactor verifies the disappearance of the esters in favour of more polar products.

The reaction media are concentrated dry under reduced pressure by Multivac. The solids obtained are triturated with acetone (10V) and then filtered on sintered material and dried under vacuum.

Step 5: Saponification

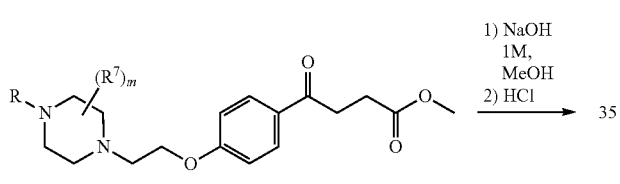

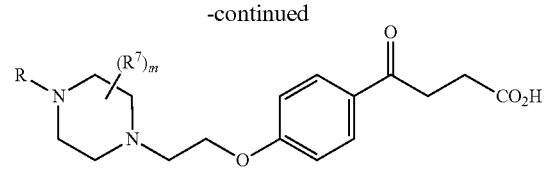

Equipment: Radley equipped with reactors and provided with magnetic agitation.

The various esters are put in solution in methanol (4V) in the presence of a 1 M soda solution (8V). After one night of agitation under these conditions, monitoring by TLC (Eluent: dichloromethane/methanol 98/2, UV revelation) verifies the disappearance of the esters in favour of more polar products.

After concentration of the methanol, the various aqueous solutions are extracted by means of ethyl acetate (5 ml) and then acidified to pH 1 by means of a 3 M hydrochloric acid solution.

The acids are next isolated by desalification producing an elution of the various aqueous solutions on Porapak Rxn resin.

Desalification Protocol:
Conditioning of the resin by 45 ml of methanol
Depositing the aqueous phase (4 to 5 ml)
Rinsing with 100 ml of methanol
Eluting with 100 ml of 2 M ammonia solution in methanol
Concentrating dry under reduced pressure The solids obtained after desalification are triturated with ethyl ether or recrystallised in acetonitrile.

EXAMPLE 2

Obtaining of the Compounds According to the Invention

The following compounds were obtained by implementation of the general diagram of example 1 (step 5 acid hydrolysis)

---

Yield: 99%    Structure: Compound 1

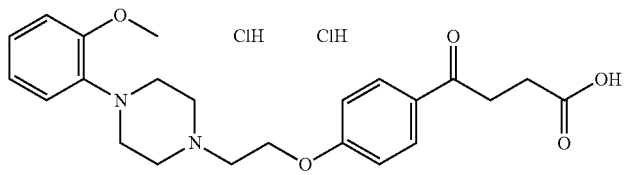 [SMILES: COc1ccccc1N1CCN(CCOc2ccc(C(=O)CCC(=O)O)cc2)CC1 ; Cl ; Cl]

Molecular mass: 485.41
Raw formula: $C_{23}H_{30}Cl_2N_2O_5$
Form/colour: White solid $^1$H NMR (DMSO, 300 MHz, δ ppm): 2.56 (t, 2H), 3.10 (t, 2H); 3.21 (t, 2H); 3.33 (q, 2H); 3.50 (d, 2H); 3.61-3.66 (m, 4H); 7.14 (d, 2H); 8.00 (d, 2H); 11.21 (s wide, 1H)

MS (ESI): 413.12 (MH$^+$); 411.10 (MH$^-$) base form

Yield: 85%    Structure: Compound 2

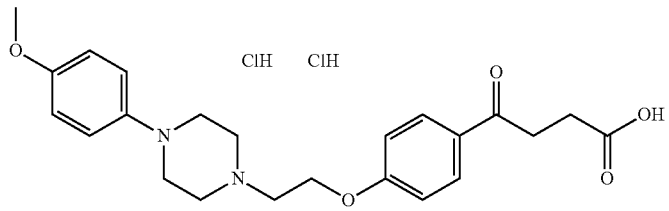 [SMILES: COc1ccc(N2CCN(CCOc3ccc(C(=O)CCC(=O)O)cc3)CC2)cc1 ; Cl ; Cl]

Molecular mass: 485.41
Raw formula: $C_{23}H_{30}Cl_2N_2O_5$
Form/colour: White solid $^1$H NMR (DMSO, 300 MHz, δ ppm): 2.56 (t, 2H), 3.12-3.23 (m, 4H); 3.23-3.35 (m, 2H); 3.59-3.70 (m, 9H); 4.58 (t, 2H); 6.87 (d, 2H); 7.00 (d, 2H); 7.14 (d, 2H); 7.99 (d, 2H); 11.38 (s wide, 1H)

MS (ESI): 413.12 (MH$^+$); 411.10 (MH$^-$) base form

Yield: 95%   Structure: Compound 3

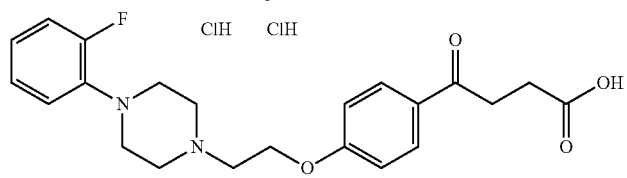

Molecular mass: 473.38
Raw formula: $C_{22}H_{27}Cl_2FN_2O_4$
Form/colour: White solid $^1$H NMR (DMSO, 300 MHz, δ ppm): 2.56 (t, 2H); 3.18-3.41 (m, 6H); 3.50 (d, 2H); 3.63-3.70 (m, 4H); 4.59 (t, 2H); 7.00-7.23 (m, 6H); 7.99 (d, 2H); 11.49 (s wide, 1H)
MS (ESI): 401.10 (MH$^+$); 399.2(MH$^-$) base form Yield: 60%   Structure: Compound 4

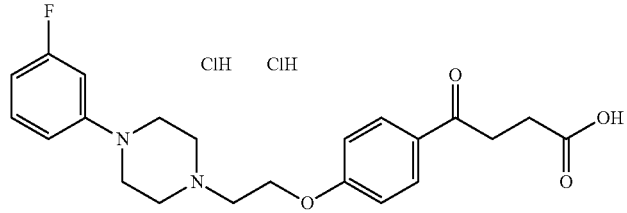 [SMILES: O=C(O)CCC(=O)c1ccc(OCCN2CCN(c3cccc(F)c3)CC2)cc1 ; Cl ; Cl]

Molecular mass: 473.38
Raw formula: $C_{22}H_{27}Cl_2FN_2O_4$
Form/colour: White solid $^1$H NMR (DMSO, 300 MHz, δ ppm): 2.56 (t, 2H); 3.18-3.41 (m, 6H); 3.59-3.66 (m, 4H); 3.70-3.93 (m, 2H); 4.53-4.59 (m, 2H); 6.63 (t, 1H); 6.82 (d, 1H); 6.87 (s, 1H); 7.14 (d, 2H); 7.26 (q, 1H); 8.00 (d, 2H); 11.25 (s wide, 1H); 12.15 (s wide, 1H)
MS (ESI): 401.20 (MH$^+$); 399.3 (MH$^-$) base form Yield: 96%   Structure: Compound 5

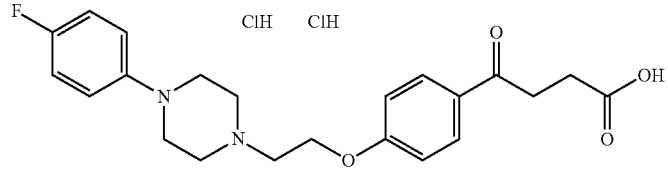 [SMILES: O=C(O)CCC(=O)c1ccc(OCCN2CCN(c3ccc(F)cc3)CC2)cc1 ; Cl ; Cl]

Molecular mass: 473.38 $C_{22}H_{27}Cl_2FN_2O_4$
Form/colour: White solid $^1$H NMR (DMSO, 300 MHz, δ ppm): 2.56 (t, 2H); 3.11-3.34 (m, 6H); 3.61-3.70 (m, 4H); 3.75 (d, 2H); 4.58 (t, 2H); 7.03-7.15 (m, 6H); 8.00 (d, 2H); 11.29 (s wide, 1H)
MS (ESI): 401.20 (MH$^+$); 399.3 (MH$^-$) base form Yield 80%   Structure: Compound 6

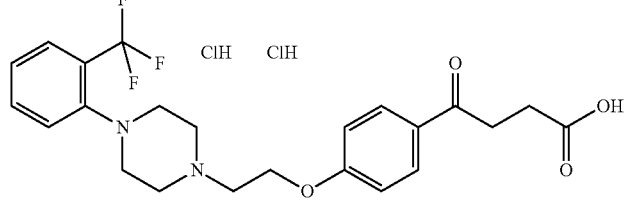

Molecular mass: 523.38
Raw formula: $C_{23}H_{27}Cl_2F_3N_2O_4$
Form/colour: Off-white solid $^1$H NMR (DMSO, 300 MHz, δ ppm): 2.56 (t, 2H); 3.10 (d, 2H); 3.21 (t, 2H); 3.28-3.38 (m, 4H); 3.62-3.72 (m, 4H); 4.54-4.60 (m, 2H); 7.14 (d, 2H); 7.41 (t, 1H); 7.56 (d, 1H); 7.72 (d, 2H); 8.00 (d, 2H); 11.32 (s wide, 1H); 12.15 (s wide, 1H)
MS (ESI): 451.20 (MH$^+$); 449.20 (MH$^-$) base form Yield: 30%   Structure: Compound 7

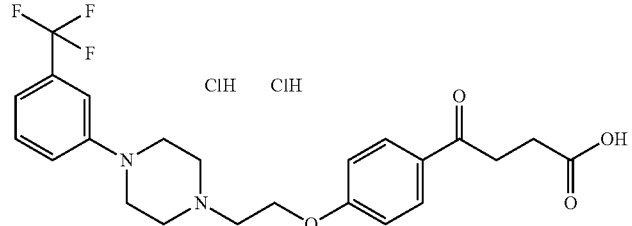

Molecular mass: 523.38
Raw Formula: $C_{23}H_{27}Cl_2F_3N_2O_4$
Form/colour: Off-white solid $^1$H NMR (DMSO, 300 MHz, δ ppm): 2.56 (t, 2H); 3.18-3.28 (m, 6H); 3.62-3.72 (m, 4H); 3.93-4.11 (m, 2H); 4.53-4.58 (m, 2H); 7.13 (d, 2H); 7.15 (d, 1H); 7.28 (d, 1H); 7.29 (d, 1H); 7.47 (t, 1H); 8.00 (d, 2H); 11.21 (s wide 1H); 12.15 (s wide, 1H)
MS (ESI): 451.20 (MH$^+$); 449.20 (MH$^-$) base form Yield: 20%    Structure: Compound 8

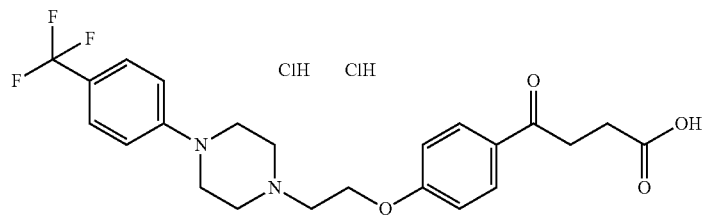 [SMILES: O=C(O)CCC(=O)c1ccc(OCCN2CCN(c3ccc(C(F)(F)F)cc3)CC2)cc1 ; Cl ; Cl]

Molecular mass: 523.38
Raw formula: $C_{23}H_{27}Cl_2F_3N_2O_4$
Form/colour: Off-white solid $^1$H NMR (DMSO, 300 MHz, δ ppm): 2.57 (t, 2H); 3.21 (t, 2H); 3.29 (d, 4H); 3.62-3.72 (m, 4H); 4.02-4.10 (m, 2H); 4.52-4.58 (m, 2H); 7.11-7.15 (m, 4H); 7.58 (d, 2H); 8.00 (d, 2H); 11.10 (s wide, 1H); 12.18 (s wide, 1H)
MS (ESI): 451.20 (MH$^+$); 449.20 (MH$^-$) base form Yield: 78%    Structure: Compound 9

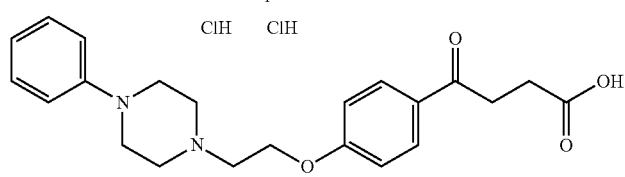

Molecular mass: 455.39
Raw formula: $C_{22}H_{28}Cl_2N_2O_4$
Form/colour: White solid $^1$H NMR (DMSO, 300 MHz, δ ppm): 2.56 (t, 2H); 3.13-3.35 (m, 6H); 3.60-3.68 (m, 4H); 3.83 (d, 2H); 4.58 (t, 2H); 6.86 (t, 1H); 7.00 (d, 2H); 7.14 (d, 2H); 7.26 (t, 2H); 8.00 (d, 2H); 11.36 (s wide, 1H)
MS (ESI): 383.20 (MH$^+$); 381.20 (MH$^-$) base form Yield: 93%    Structure: Compound 10

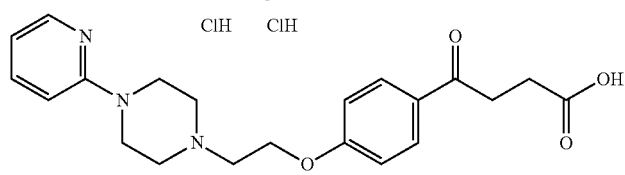 [SMILES: O=C(O)CCC(=O)c1ccc(OCCN2CCN(c3ccccc3)CC2)cc1 ; Cl ; Cl]

Molecular mass: 456.37
Raw formula: $C_{21}H_{27}Cl_2N_3O_4$
Form/colour: White solid $^1$H NMR (DMSO, 300 MHz, δ ppm): 2.56 (t, 2H); 3.18-3.32 (m, 4H); 3.42-3.52 (m, 2H); 3.62-3.72 (m, 4H); 4.45 (d, 2H); 4.55 (t, 2H); 6.88 (t, 1H); 7.12-7.18 (m, 3H); 7.80-7.85 (m, 1H); 8.00 (d, 2H); 8.14 (d, 1H); 11.24 (s wide, 1H)
MS (ESI): 384.30 (MH$^+$); 382.20 (MH$^-$) base form Yield: 99%    Structure: Compound 11

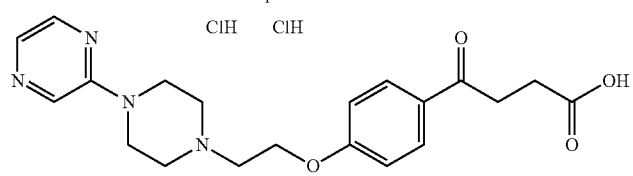

Raw formula: $C_{20}H_{26}Cl_2N_4O_4$
Form/colour: Yellow solid $^1$H NMR (DMSO, 300 MHz, δ ppm): 2.56 (t, 2H); 3.18-3.28 (m, 4H); 3.45 (t, 2H); 3.58-3.67 (m, 4H); 4.47 (d, 2H); 4.57 (t, 2H); 7.13 (d, 2H); 7.96 (d, 1H); 8.00 (d, 2H); 8.18 (dd, 1H); 8.45 (dd, 1H); 11.52 (s wide, 1H)
MS (ESI): 385.20 (MH$^+$); 383.20 (MH$^-$) base form Yield: 99%    Structure: Compound 12

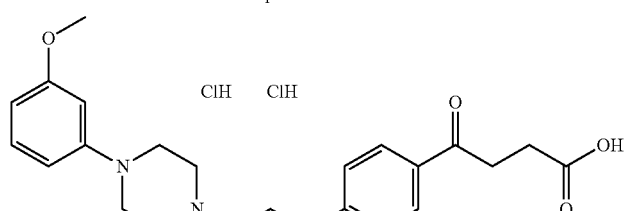

Molecular mass: 485.41
Raw formula: $C_{23}H_{30}Cl_2N_2O_5$
Form/colour: White solid $^1$H NMR (DMSO, 300 MHz, δ ppm): 2.56 (t, 2H); 3.12-3.33 (m, 6H); 3.61-3.67 (m, 4H); 3.73 (s, 3H); 3.84 (d, 2H); 4.57 (t, 2H); 6.45 (dd, 1H); 6.53 (s, 1H); 6.58 (dd, 1H); 7.10-7.19 (m, 3H); 8.00 (d, 2H); 11.21 (s wide, 1H)
MS (ESI): 413.20 (MH$^+$); 411.20 (MH$^-$) base form Yield: 70%  Structure: Compound 13

Molecular mass: 480.40
Raw formula: $C_{23}H_{27}Cl_2N_3O_4$
Form/colour: White solid $^1$H NMR (DMSO, 300 MHz, δ ppm): 2.57 (t, 2H); 3.20 (t, 2H); 3.25-3.35 (m, 4H); 3.62-3.66 (m, 4H); 4.05-4.12 (m, 2H); 4.52-4.54 (m, 2H); 7.12 (dd, 4H); 7.67 (d, 2H); 8.00 (d, 2H); 10.79 (s wide, 1H); 12.10 (s, wide, 1H)
MS (ESI): 408.10 (MH$^+$); 406.00 (MH$^-$) base form Yield: 50%  Structure: Compound 14

Molecular Mass: 519.45
Raw formula: $C_{22}H_{28}Cl_2N_2O_6S$
Form/colour: White solid $^1$H NMR (DMSO, 300 MHz, δ ppm): 2.56 (t, 2H); 2.76 (t, 2H); 3.19 (t, 2H); 3.25-3.31 (m, 2H); 3.53-3.84 (m, 6H); 4.46 (t, 2H); 7.07 (d, 2H); 7.67-7.80 (m, 5H); 7.97 (d, 2H); 11.08 (s wide, 1H); 12.13 (s wide, 1H)
MS (ESI): 447.00 (MH$^+$); 444.90 (MH$^-$) base form Yield: 67%  Structure: Compound 15

Molecular mass: 457.38
Raw formula: $C_{17}H_{26}Cl_2N_2O_6S$
Form/colour: White solid $^1$H NMR (DMSO, 300 MHz, δ ppm): 2.56 (t, 2H); 3.02 (s, 3H); 3.20 (t, 2H); 3.26-3.76 (m, 10H); 4.53 (t, 2H); 7.11 (d, 2H); 7.98 (d, 2H); 11.38 (s wide, 1H) ; 12.15 (s wide, 1H)
MS (ESI): 385.00 (MH$^+$); 383.10 (MH$^-$) base form Yield: 74%  Structure: Compound 16

Molecular mass: 551.47
Mass:
Raw formula: $C_{23}H_{29}Cl_2N_2O_6S$
Form/colour: White solid $^1$H NMR (DMSO, 300 MHz, δ ppm): 2.56 (t, 2H); 3.19-3.23 (m, 6H); 3.31-3.37 (m, 4H); 3.64-3.75 (m, 5H); 4.53 (t, 2H); 7.14 (d, 2H); 7.33 (t, 1H); 7.68 (d, 1H); 7.74 (d, 1H); 8.00 (d, 2H); 10.80 (s wide, 1H) ; 12.14 (s wide, 1H)
MS (ESI): 479.00 (MH$^+$); 476.90 (MH$^-$) base form Yield: 60%  Structure: Compound 17

Molecular mass: 513.45
Raw formula: $C_{22}H_{26}Cl_2N_4O_4S$
Form/colour: White solid $^1$H NMR (DMSO, 300 MHz, δ ppm): 2.57 (t, 2H); 3.21 (t, 2H); 3.37-4.05 (m, 8H); 4.57 (t, 2H); 4.87-4.90 (m, 2H); 7.14 (d, 2H); 7.65 (d, 1H); 8.00 (d, 2H); 8.59 (d, 1H); 8.89 (s, 1H); 12.10 (s wide, 1H)
MS (ESI): 441.00 (MH$^+$); 439.00 (MH$^-$) base form Yield: 69%  Structure: Compound 18

Molecular mass: 462.40
Raw formula: $C_{19}H_{25}Cl_2N_3O_4S$
Form/colour: White solid $^1$H NMR (DMSO, 300 MHz, δ ppm): 2.57 (t, 2H); 3.21 (t, 2H); 3.29-3.38 (m, 2H); 3.54 (t, 2H); 3.63-3.70 (m, 4H); 4.05 (d, 2H); 4.54 (t, 2H); 7.01 (d, 1H); 7.13 (d, 2H); 7.26 (d, 1H); 8.00 (d, 2H); 11.21 (s wide, 1H)
MS (ESI): 390.00 (MH$^+$); 388.00 (MH$^-$) base form The following compounds were obtained using the general diagram of example 5 (step 5 saponification)

---

Yield: 55%   Structure: Compound 19

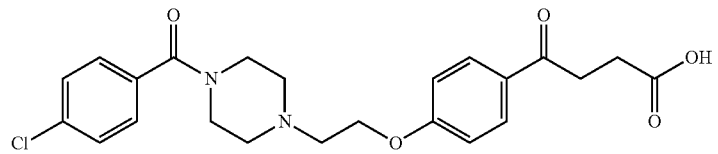 [SMILES: O=C(O)CCC(=O)c1ccc(OCCN2CCN(C(=O)c3ccc(Cl)cc3)CC2)cc1]

Molecular mass: 444.92
Raw formula: $C_{23}H_{25}ClN_2O_5$
Form/colour: White solid $^1$H NMR (DMSO, 300 MHz, δ ppm): 2.41 (t, 2H); 2.44-2.57 (m, 4H); 2.76 (t, 2H); 3.11 (t, 2H); 3.28-3.38 (m, 2H); 3.59-3.66 (m, 2H); 4.17 (t, 2H); 7.04 (d, 2H); 7.47 (dd, 4H); 7.93 (d, 2H)
MS (ESI): 444.90 (MH)$^+$; 442.90 (MH$^-$)

Yield: 50%   Structure: Compound 20

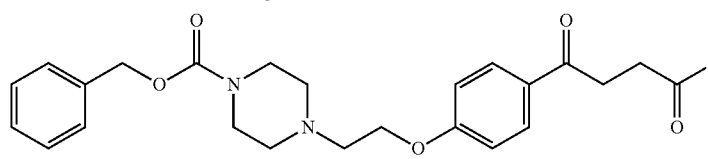

Molecular mass: 440.50
Raw formula: $C_{24}H_{28}N_2O_6$
Form/colour: White solid $^1$H NMR (DMSO, 300 MHz, δ ppm): 2.40 (t, 2H); 2.44-2.51 (m, 4H); 2.74 (t, 2H); 3.09 (t, 2H); 3.36-3.40 (m, 4H); 4.16 (t, 2H); 5.07 (s, 2H); 7.04 (d, 2H); 7.29-7.40 (m, 5H); 7.92 (d, 2H)
MS (ESI): 440.90 (MH$^+$); 438.90 (MH$^-$)

Yield: 47%   Structure: Compound 21

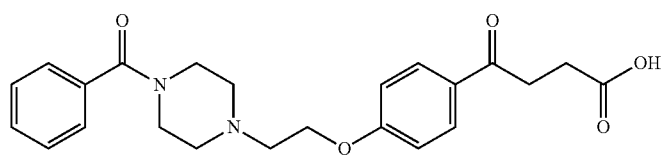 [SMILES: O=C(O)CCC(=O)c1ccc(OCCN2CCN(C(=O)c3ccccc3)CC2)cc1]

Molecular mass: 410.47
Raw formula: $C_{23}H_{26}N_2O_5$
Form/colour: White solid $^1$H NMR (DMSO, 300 MHz, δ ppm): 2.37 (t, 2H); 2.44-2.58 (m, 4H); 2.76 (t, 2H); 3.09 (t, 2H); 3.29-3.39 (m, 2H); 3.57-3.66 (m, 2H); 4.18 (t, 2H); 7.04 (d, 2H); 7.36-7.47 (m, 5H); 7.92 (d, 2H)
MS (ESI): 470.90 (MH$^+$); 408.90 (MH$^-$)

Yield: 21%   Structure: Compound 22

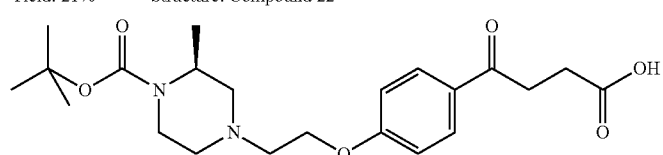

Molecular mass: 420.51
Raw formula: $C_{22}H_{32}N_2O_6$
Form/colour: White solid $^1$H NMR (DMSO, 300 MHz, δ ppm): 1.12 (d, 3H); 1.39 (s, 9H); 1.97 (td, 1H); 2.15 (dd, 1H); 2.39 (t, 2H); 2.65-2.78 (m, 3H); 2.84-3.02 (m, 2H); 3.10 (t, 2H); 3.66 (d, 1H); 4.03-4.11 (m, 1H); 4.17 (t, 2H); 7.05 (d, 2H); 7.93 (d, 2H)
MS (ESI): 421.00 (MH$^+$); 419.00 (MH$^-$)

Yield: 20%   Structure: Compound 23

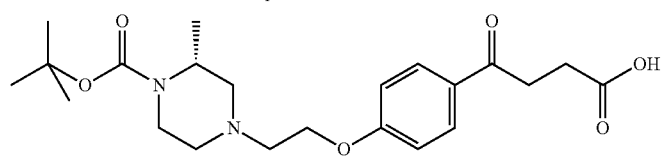

Molecular mass: 420.51
Raw formula: $C_{22}H_{32}N_2O_6$
Form/colour: White solid $^1$H NMR (DMSO, 300 MHz, δ ppm): 1.12 (d, 3H); 1.39 (s, 9H); 1.97 (td, 1H); 2.15 (dd, 1H); 2.38 (t, 2H); 2.66-2.77 (m, 3H); 2.84-3.02 (m, 2H); 3.09 (t, 2H); 3.65 (d, 1H); 4.02-4.10 (m, 1H); 4.16 (t, 2H); 7.03 (d, 2H); 7.93 (d, 2H)
MS (ESI): 421.00 (MH$^+$); 419.00 (MH$^-$)

EXAMPLE 3
General Diagram for Preparing Compounds for which $R^1$ Represents —C(OH)HCR$^3$R$^4$CR$^5$R$^6$C(O)OH or
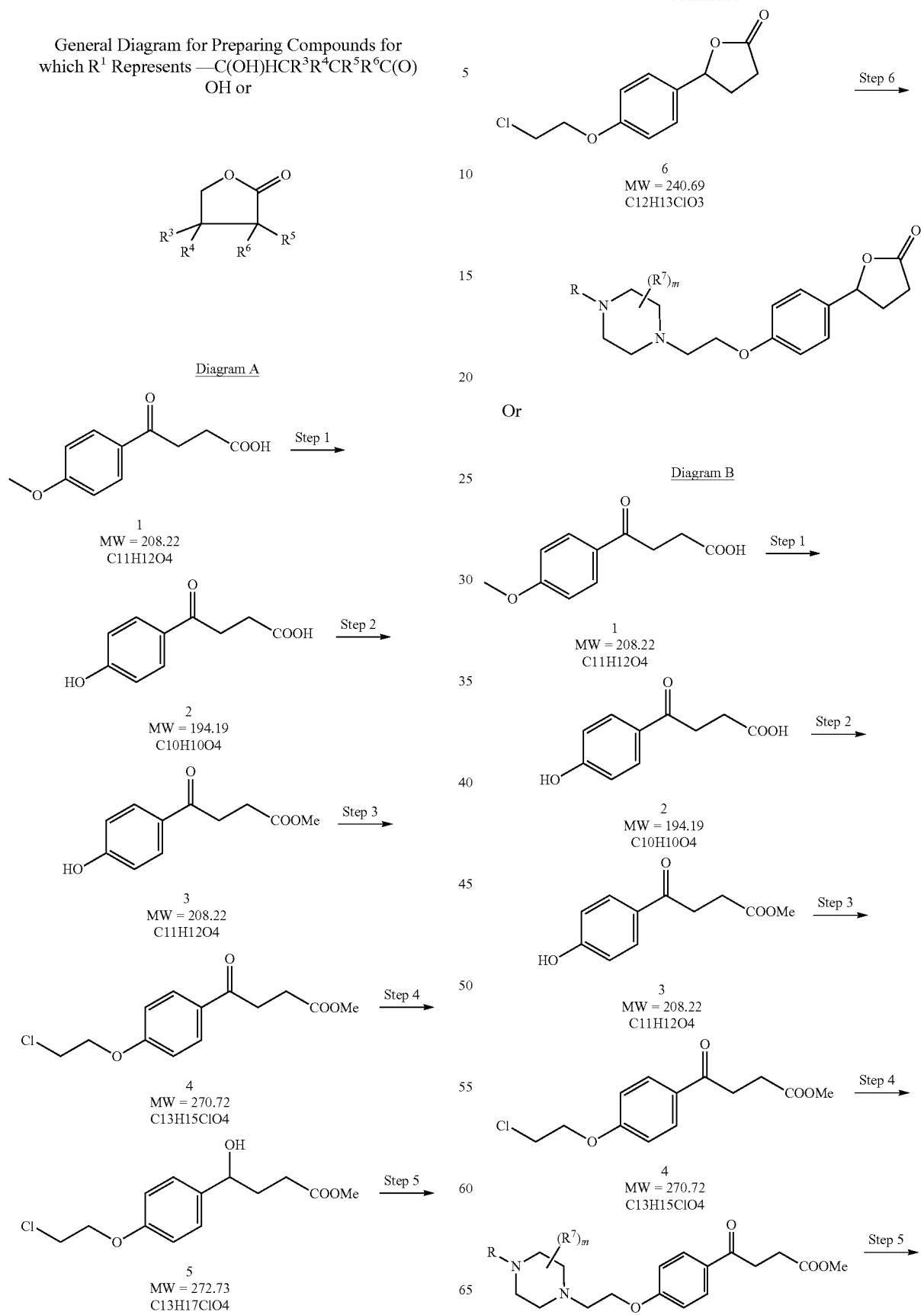

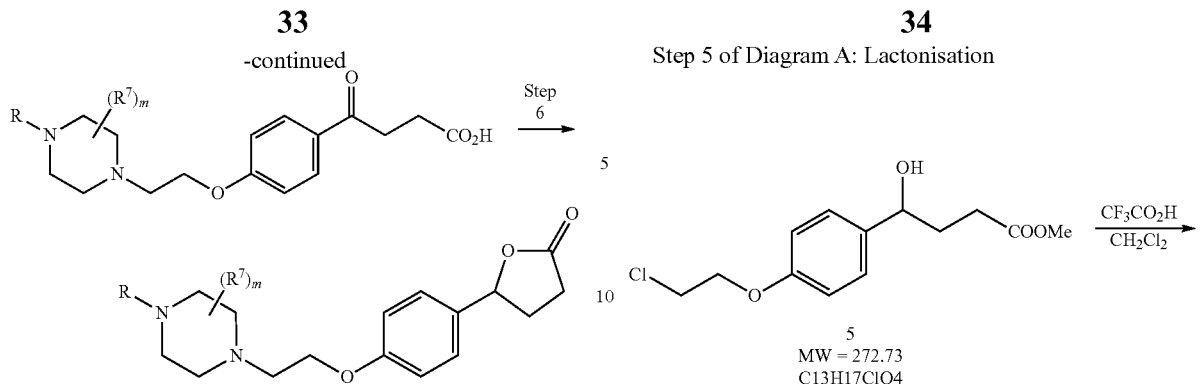

Steps 1 to 3 of diagrams A and B correspond to steps 1 to 3 of the diagram of example 1. Steps 4 and 5 of diagram B correspond to steps 4 and 5 of the diagram of example 1.

Step 4 of Diagram A: Reduction of the 4-Oxo Function

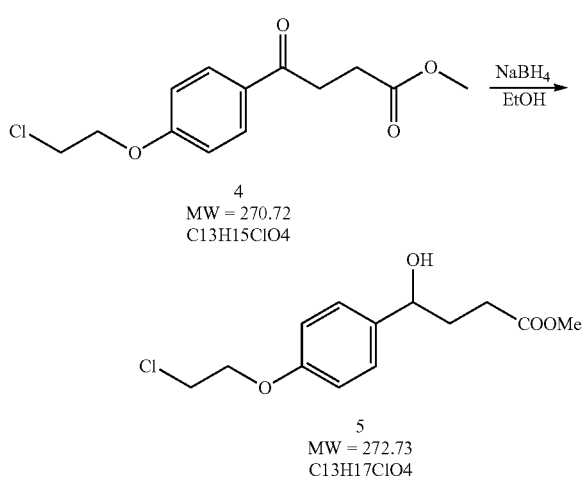

Equipment: 100 ml three-necked flask equipped with magnetic agitation and placed under nitrogen scavenging.

The chlorine derivative 4 (5 g, 18.5 mmol, 1 eq.) is put in suspension in absolute ethanol (50 ml). Sodium tetraborohydride (2.8 g, 74 mmol), 4 eq.) is added, in portions over a period of 15 minutes, to the suspension previously cooled to 0° C. by means of a brine bath. At the end of the addition the brine bath is removed and the reaction medium is left under agitation at ambient temperature.

The advancement of the reaction is monitored by TLC (eluent: heptane/ethyl acetate: 1/1). After an hour and a quarters agitation the disappearance of the starting ketone 4 is observed in favour of the formation of two more polar products.

The ethanol is eliminated by evaporation under reduced pressure. The residue obtained is taken up by a water/ice mixture and acidified, at pH 2, by the slow addition of a 3N hydrochloric acid solution. The aqueous phase is next extracted three times by means of ethyl acetate. Once collected together, the organic phase are washed once with a saturated sodium chloride solution, dried on magnesium sulphate, filtered and then concentrated under reduced pressure in order to provide a yellow oil (4.5 g).

$^1$HNMR analysis of the raw reaction substance reveals the presence of the expected alcohol 5 in a mixture with the lactone form 6. The raw reaction substance is engaged in cyclisation without a purification step.

Step 5 of Diagram A: Lactonisation

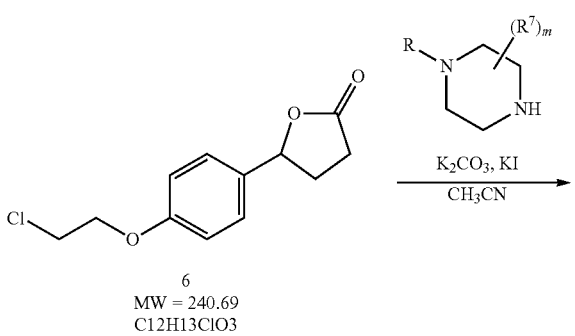

Equipment: 100 ml three-necked flask equipped with mechanical agitation and a refrigerant and placed under nitrogen scavenging.

The alcohol/lactone mixture 5/6 (4.5 g) is put in solution in dichloromethane (30 ml) in the presence of trifluoroacetic acid (0.2 ml). The solution is heated to reflux for 6 hours.

The advancement of the reaction is monitored by TLC (eluent: heptane/ethyl acetate: 1/1). The reaction is not total but does not change any further.

The heating is cut off. After return of the reaction medium to ambient temperature, the dichloromethane phase is washed successively with a saturated sodium hydrogenocarbonate solution and then with water. The organic phase is dried on magnesium sulphate, filtered and then concentrated under reduced pressure in order to provide a white wax (3.8 g).

The waxy residue is purified by chromatography on pre-packed column (80 g). The compounds to be separated are eluted using a heptane/ethyl acetate gradient.

The required compound is isolated in the form of a white solid (1.3 g).

Yield over the two steps 29%

Step 6 of Diagram A: Nucleophilic Substitution Reaction

35
-continued

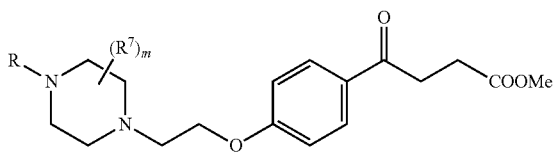

Equipment: Schlenk tube (25 ml) equipped with mechanical agitation.

Under nitrogen scavenging, the chlorine derivative 6 (1 eq.) is put in solution in acetonitrile (4 ml) in the presence of R-piperazine (10V), potassium carbonate (3 eq.) previously dried, and potassium iodide (1 eq.). After nitrogen scavenging has been carried out, the reactor is closed and heated at 80° C. for 72 hours.

After 72 hours, the heating is stopped. After return to ambient temperature, the reaction medium is filtered on Supelco cartridge in order to eliminate the inorganic salts. After rinsing with acetonitrile, the filtrate is concentrated dry under reduced pressure. The residue obtained is taken up with ethyl acetate and washed twice with water. The organic phase is dried on magnesium sulphate, filtered and then concentrated under reduced pressure.

The raw reaction substance is purified by chromatography on Redisep 40 g prepacked column, Biotage SP4 system, using a dichloromethane/methanol gradient.

EXAMPLE 4

Obtaining of Compounds of Formula (I) According to the Invention

The following compounds were obtained using the method according diagram A of example 3.

The following compound was obtained using the method according to diagram B of example 3, step 6 being performed as follows:

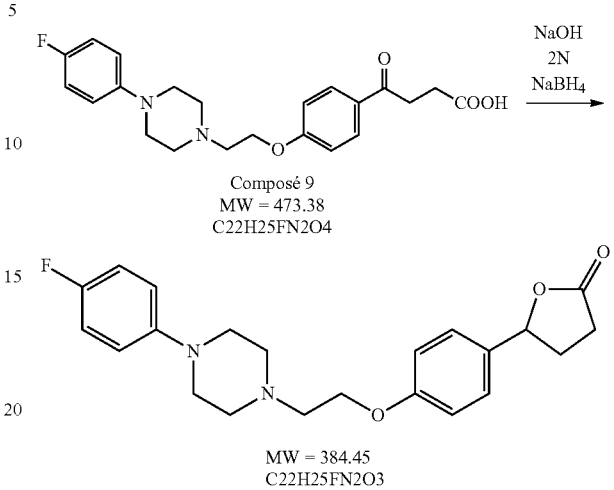

Composé 9
MW = 473.38
$C_{22}H_{25}FN_2O_4$

MW = 384.45
$C_{22}H_{25}FN_2O_3$

Equipment: 25 ml three-necked flask equipment with mechanical agitation and placed under nitrogen scavenging.

Compound 9 (0.25 g, 0.528 mmol, 1 eq.) is put into suspension in water (7.5 ml) and then in solution by adding a 2N soda solution (1.5 ml). Sodium tetraborohydride (24 mg, 0.324 mmol, 1.2 eq.) is added to the solution. The reaction medium is left under agitation at ambient temperature overnight.

The advancement of the reaction is monitored by TLC (eluent: dichloromethane/methanol: 95/5).

The reaction medium is washed with dichloromethane. The aqueous phase is acidified to pH 1 by means of a molar solution of acid chloride and then extracted twice with dichlo-

---

Yield: 70%  Structure: Compound 24

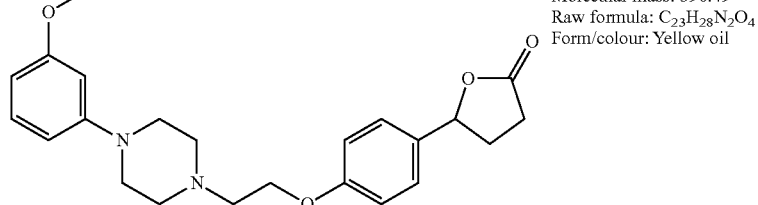

Molecular mass: 396.49
Raw formula: $C_{23}H_{28}N_2O_4$
Form/colour: Yellow oil $^1$H NMR (DMSO, 300 MHz, δ ppm): 2.15-2.28 (m, 1H); 2.58-2.71 (m, 3H); 2.75-2.85 (m, 4H); 2.91 (t, 2H); 3.26 (dd, 4H); 3.80 (s, 3H); 4.19 (t, 2H); 5.45-5.51 (m,1H); 6.44 (dd, 1H); 6.48 (t, 1H); 6.57 (dd, 1H); 6.95 (dd, 2H); 7.19 (t, 1H); 7.28 (d, 2H)
MS (ESI+): 397.3 (MH$^+$)

Yield: 30%  Structure: Compound 25

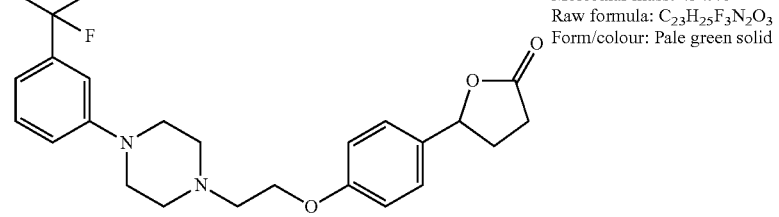

Molecular mass: 434.46
Raw formula: $C_{23}H_{25}F_3N_2O_3$
Form/colour: Pale green solid $^1$H NMR (DMSO, 300 MHz, δ ppm): 2.16-2.29 (m, 1H); 2.58-2.71 (m, 3H); 2.78-2..83 (m, 4H); 2.93 (t, 2H); 3.31(dd, 4H); 4.20 (t, 2H); 5.46-5.51 (m, 1H); 6.96 (d, 2H); 7.06-7.14 (m, 3H); 7.29 (d, 2H); 7.37 (t, 1H)
MS (ESI+): 435.3 (MH$^+$)

romethane. The product being partially soluble in water, the acidic aqueous phase is concentrated dry under reduced pressure. The salts are taken up in a minimum amount of water and the product is extracted twice with dichloromethane. The various dichloromethane phases are collected together, dried on magnesium sulphate, filtered and concentrated under reduced pressure in order to provide a white meringue (0.2 g).

The raw reaction substance is purified by chromatography on Redisep 15 g prepacked column, Biotage SP4 system, using a dichloromethane/methanol gradient. Yield 60%

Yield: 60%  Structure: Compound 26

Molecular mass: 384.45
Raw formula: $C_{22}H_{25}FN_2O_3$
Form/colour: White solid $^1$H NMR (DMSO, 300 MHz, δ ppm): 2.14-2.25 (m, 1H); 2.58-2.70 (m, 3H); 3.30-3.50 (m, 10H); 4.48-4.55 (m, 2H); 5.44-5.50 (m, 1H); 6.89-7.03 (m, 6H); 7.29 (d, 1H); 7.31 (d, 1H)
MS (ESI+): 385.3 (MH$^+$)

EXAMPLE 5

Study of the Antidiabetic Activity in db/db Mouse

The antidiabetic activity of the compounds of formula (I) orally on a type 2 diabetes animal model, the db/db mouse, was tested.

Diabetic mice are used at the age of 8 weeks; they then have very high hyperglycaemia. The animals are stabilised at a minimum for one week after reception and up to the day of experimentation in an animal house at a temperature regulated at 21°-22° C. and subjected to a fixed cycle of light (from 7 a.m. to 7 p.m.) and darkness (from 7 p.m. to 7 a.m.). Their food consisted of a maintenance regime; water and food were supplied "ad libitum".

The mice are treated orally with the product to be tested (200 mg/kg per os) in suspension in a mixture of water and methyl cellulose or the vehicle (mixture of water and methyl cellulose) in the morning of the day of the experimentation. Just before the administration of the product and one and two hours after the administration of the product, a blood sample (one drop of blood) is taken following a small incision in the tail for determining glycaemia.

This glycaemia is measured by means of a glucometer (Lifescan OneTouch Ultra, LifeScan, Johnson-Johnson Company) and OneTouchUltra glycaemia measurement strips.

Table 1 contains the results obtained. These results express the percentage drop in the initial glycaemia. For comparison, the drop in the glycaemia is also reported for control animals that did not receive the vehicle and for metformin.

|  | Drop in glycaemia (in % of the initial value) | |
|---|---|---|
|  | After 1 hour | After 2 hours |
| Controls | 4 | 12 |
| Compound 2 | 7 | 12 |
| Compound 3 | 23 | 29 |
| Compound 4 | 9 | 20 |
| Compound 5 | 5 | 23 |
| Compound 9 | 7 | 34 |
| Compound 10 | 23 | 39 |
| Compound 12 | 19 | 32 |
| Metformin | 22 | 27 |

These results show the efficacy of the compounds of formula (I) for causing a reduction in glycaemia in diabetic animals.

The invention claimed is:

1. A compound of formula (I)

(I)

in which:
$R^1$ represents:
a —C(O)CR$^3$R$^4$CR$^5$R$^6$C(O)OH group;
a —C(OH)(H)CR$^3$R$^4$CR$^5$R$^6$C(O)OH group; or
a group n represents 0 or 1; m represents an integer ranging from 0 to 8;
$L^1$ represents a —C(O)—; —C(O)O— or —S(O)$_2$— group;
$R^2$ represents:
a carbocycle group with 5, 6 or 7 members, saturated, partially unsaturated or aromatic, substituted or non-substituted;
a polycarbocycle group with 8 to 14 members, saturated, partially unsaturated or aromatic, substituted or non-substituted;
a heterocycle group with 5, 6 or 7 members, substituted or non-substituted, saturated, partially unsaturated or aromatic, comprising 1, 2 or 3 heteroatoms, identical or different;

a polyheterocycle group with 8 to 14 members, substituted or non-substituted, saturated, partially unsaturated or aromatic, comprising 1, 2 or 3 heteroatoms identical or different;

a -$L^2$-carbocycle group, the carbocycle being in 5, 6 or 7 members, saturated, partially unsaturated or aromatic, substituted or non-substituted;

a -$L^2$-polycarbocycle, the polycarbocycle being in 8 to 14 members, saturated, partially unsaturated or aromatic, substituted or non-substituted;

a -$L^2$-heterocycle group, the heterocycle being in 5, 6 or 7 members, substituted or non-substituted, saturated, partially unsaturated or aromatic and comprising 1, 2 or 3 heteroatoms, identical or different;

a -$L^2$-polyheterocycle group, the polyhetero cycle being in 8 to 14 members, substituted or non-substituted, saturated, partially unsaturated or aromatic and comprising 1, 2 or 3 hetero atoms, identical or different; or a hydrocarbon group, linear or branched, $C_1$ to $C_5$;

$L^2$ represents an alkyl, linear or branched, $C_1$ to $C_5$;

$R^3$, $R^4$, $R^5$ and $R^6$, identical or different, represent:

a hydrogen atom;

an alkyl group, linear or branched, $C_1$ to $C_5$;

a carbocycle group with 5, 6 or 7 members, saturated, partially unsaturated or aromatic, substituted or non-substituted;

or $R_3$ and $R_4$ form together with the carbon atom to which they are bonded a carbocycle with 5, 6 or 7 members, substituted or non-substituted;

or $R_5$ and $R_6$ form together with the carbon atom to which they are bonded a carbocycle with 5, 6 or 7 members, substituted or non-substituted; or $R^7$, identical or different, represents:

an alkyl, linear or branched, $C_1$ to $C_5$;

a -$L^2$-carbocycle group, the carbocycle being in 5, 6 or 7 members, saturated, partially unsaturated or aromatic, substituted or non-substituted;

a -$L^2$-polycarbocycle, the polycarbocycle being in 8 to 14 members, saturated, partially unsaturated or aromatic, substituted or non-substituted;

a -$L^2$-heterocycle group, the heterocycle being in 5, 6 or 7 members, substituted or non-substituted, saturated, partially unsaturated or aromatic and comprising 1, 2 or 3 heteroatoms, identical or different, in particular chosen from nitrogen, oxygen or sulphur; or a -$L^2$-polyheterocycle group, the polyheterocycle being in 8 to 14 members, substituted or non-substituted, saturated, partially unsaturated or aromatic and comprising 1, 2 or 3 heteroatoms, identical or different, in particular chosen from nitrogen, oxygen or sulphur; isomers, enantiomers and diastereoisomers thereof and the addition salts thereof with pharmaceutically acceptable bases or acids.

2. A compound according to claim 1, for which the carbocycle, substituted or non-substituted, is in 6 aromatic members, the polycarbocycle, substituted or non-substituted, is in 9 or 10 members, the heterocycle, substituted or non-substituted, is in 5 or 6 members and comprises 1, 2 or 3 heteroatoms, and the polyheterocycle, substituted or non-substituted, is in 9 or 10 members and comprises 1, 2 or 3 heteroatoms.

3. A compound according to claim 1, for which the carbocycles, polycarbocycles, heterocycles and polyheterocycles are non-substituted or substituted by one or more substituents, identical or different, chosen from:

a $C_1$ to $C_6$ alkoxy group, linear or branched;

a halogen atom;

a $C_1$ to $C_5$ linear or branched hydrocarbon group;

a $C_1$ to $C_5$ linear or branched hydrocarbon group, substituted by one or more halogen atoms;

a cyano group (—CN);

a carbocycle group in 5, 6 or 7 members, saturated, partially unsaturated or aromatic, substituted or non-substituted; or a sulfonylalkyl group (—S(O)$_2$-alkyl), in which the alkyl is linear or branched, $C_1$ to $C_5$.

4. The compound according to claim 1, in which $R^2$ represents a 6-member aromatic carbocycle group, non-substituted or substituted by one or more substituents, identical or different, chosen from:

a $C_1$ to $C_6$ alkoxy group, linear or branched;

a halogen atom;

a $C_1$ to $C_5$ alkyl group, linear or branched;

a $C_1$ to $C_5$ alkyl group, linear or branched, substituted by one or more halogen atoms;

a cyano group (—CN);

an aryl group, substituted or non-substituted by one or more substituents, identical or different, chosen from a halogen atom, a $C_1$ to $C_6$ alkoxy group, linear or branched; a $C_1$ to $C_5$ alkyl group, linear or branched;

a sulfonylalkyl group (—S(O)$_2$-alkyl), in which the alkyl is linear or branched, $C_1$ to $C_5$;

a 5 or 6 member aromatic heterocycle group, comprising 1 or 2 heteroatoms, identical or different, non-substituted or substituted by one or more substituents, identical or different, chosen from:

a $C_1$ to $C_6$ alkoxy group, linear or branched;

a halogen atom;

a $C_1$ to $C_5$ alkyl group, linear or branched;

a $C_1$ to $C_5$ alkyl group, linear or branched, substituted by one or more halogen atoms;

a cyano group (—CN);

an aryl group, substituted or non-substituted by one or more substituents, identical or different, chosen from a halogen atom, a $C_1$ to $C_6$ alkoxy group, linear or branched; a $C_1$ to $C_5$ alkyl group, linear or branched; or a sulfonylalkyl group (—S(O)$_2$-alkyl), in which the alkyl is linear or branched, $C_1$ to $C_5$;

an 8 to 14 member aromatic polyheterocycle, comprising 1 to 3 heteroatoms, identical or different, non-substituted or substituted by one or more substituents, identical or different, chosen from:

a $C_1$ to $C_6$ alkoxy group, linear or branched;

a halogen atom;

a $C_1$ to $C_5$ alkyl group, linear or branched;

a $C_1$ to $C_5$ alkyl group, linear or branched, substituted by one or more halogen atoms;

a cyano group (—CN);

a sulfonylalkyl group (—S(O)$_2$-alkyl), in which the alkyl is linear or branched, $C_1$ to $C_5$;

an aryl group, substituted or non-substituted by one or more substituents, identical or different, chosen from a halogen atom, a $C_1$ to $C_6$ alkoxy group, linear or branched; a $C_1$ to $C_5$ alkyl group, linear or branched;

a $C_1$ to $C_5$ alkyl group, linear or branched;

an -Alk-carbocycle group, the carbocycle being aromatic in 5 or 6 members, non-substituted or substituted by one or more substituents, identical or different, chosen from:

a $C_1$ to $C_6$ alkoxy group, linear or branched;

a halogen atom;

a $C_1$ to $C_5$ alkyl group, linear or branched;

a $C_1$ to $C_5$ alkyl group, linear or branched, substituted by one or more halogen atoms;

a cyano group (—CN);
a sulfonylalkyl group (—S(O)$_2$-alkyl), in which the alkyl is linear or branched, $C_1$ to $C_5$;
an aryl group, substituted or non-substituted by one or more substituents, identical or different, chosen from a halogen atom, a $C_1$ to $C_6$ alkoxy group, linear or branched; a $C_1$ to $C_5$ alkyl group, linear or branched; or Alk being a $C_1$ to $C_5$ alkyl group, linear or branched.

5. The compound according to claim 1, for which $R^2$ represents:
a phenyl, non-substituted or substituted by one or more substituents, identical or different, chosen from:
a $C_1$ to $C_6$ alkoxy group, linear or branched;
a halogen atom;
a $C_1$ to $C_5$ alkyl group, linear or branched;
a $C_1$ to $C_5$ alkyl group, linear or branched, substituted by one or more halogen atoms;
a cyano group (—CN);
a sulfonylalkyl group (—S(O)$_2$-alkyl), in which the alkyl is linear or branched, $C_1$ to $C_5$;
an aryl group, substituted or non-substituted by one or more substituents, identical or different, chosen from a halogen atom, a $C_1$ to $C_6$ alkoxy group, linear or branched; a $C_1$ to $C_5$ alkyl group, linear or branched;
a monocyclic or polycyclic heteroaryl chosen from

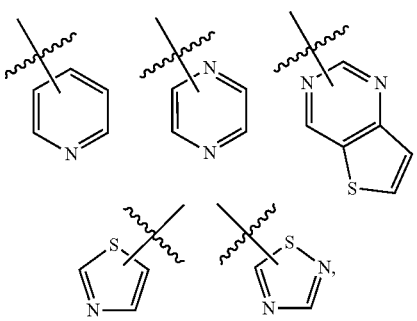

non-substituted or substituted by one or more substituents, identical or different, chosen from:
a $C_1$ to $C_6$ alkoxy group, linear or branched;
a halogen atom;
a $C_1$ to $C_5$ alkyl group, linear or branched;
a $C_1$ to $C_5$ alkyl group, linear or branched, substituted by one or more halogen atoms;
a cyano group (—CN);
a sulfonylalkyl group (—S(O)$_2$-alkyl), in which the alkyl is linear or branched, $C_1$ to $C_5$;
an aryl group, substituted or non-substituted by one or more substituents, identical or different, chosen from a halogen atom, a $C_1$ to $C_6$ alkoxy group, linear or branched; a $C_1$ to $C_5$ alkyl group, linear or branched;
an -Alk-carbocycle group, the carbocycle being a phenyl, non-substituted or substituted by one or more substituents, identical or different, chosen from:
a $C_1$ to $C_6$ alkoxy group, linear or branched;
a halogen atom;
a $C_1$ to $C_5$ alkyl group, linear or branched;
a $C_1$ to $C_5$ alkyl group, linear or branched, substituted by one or more halogen atoms;
a cyano group (—CN);
a sulfonylalkyl group (—S(O)$_2$-alkyl), in which the alkyl is linear or branched, $C_1$ to $C_5$; or
an aryl group, substituted or non-substituted by one or more substituents, identical or different, chosen from a halogen atom, a $C_1$ to $C_6$ alkoxy group, linear or branched; a $C_1$ to $C_5$ alkyl group, linear or branched;
Alk being a $C_1$ to $C_5$ alkyl, linear or branched; or
a $C_1$ to $C_5$ alkyl group, linear or branched.

6. The compound according to claim 1, in which $R^3$, $R^4$ each represents a hydrogen atom, and $R^5$ and $R^6$, identical or different, represent:
a hydrogen atom;
a $C_1$ to $C_5$ linear or branched alkyl group;
a carbocycle in 5, 6 or 7 members, saturated, partially unsaturated or aromatic; or
$R^3$ and $R^4$ form together with the carbon atom to which they are bonded a carbocycle in 5, 6 or 7 members, substituted or non-substituted; or
$R^5$ and $R^6$ form together with the carbon atom to which they are bonded a carbo cycle in 5, 6 or 7 members, substituted or non-substituted.

7. The compound according to claim 1, wherein $R^1$ represents a group C(O)CR$^3$R$^4$CR$^5$R$^6$C(O)OH.

8. The compound according to claim 1, wherein n=0.

9. The compound according to claim 1, wherein n=1.

10. A method (P1) for preparing a compound according to claim 1, the method comprising:
(a) protecting an acid function (carried by $R^1$) of a compound of formula (II)

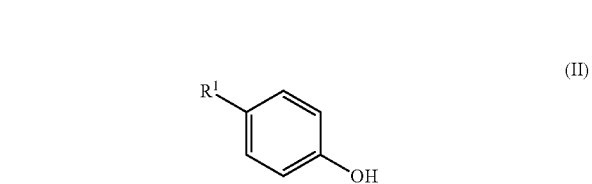

in which $R^1$ represents —C(O)CR$^3$R$^4$CR$^5$R$^6$C(O)OH; $R^3$, $R^4$, CR$^5$ and $R^6$ are as defined by claim 1;
(b) reacting a compound obtained in step (a) with a compound of formula R$^9$—(CH$_2$)$_2$—R$^8$ in which R$^8$ and R$^9$, identical or different, represent a leaving group;
(c) reacting a compound obtained at in step (c) with a compound of formula (III)

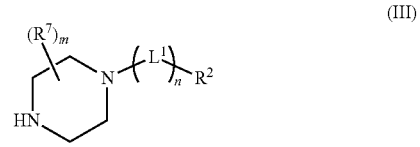

in which $L^1$, n, m, $R^2$ and $R^7$ are as defined by claim 1; and
(d) deprotecting a compound obtained at in step (c).

11. A method (P2) for preparing the compound according to claim 1, the method comprising:
(i) reacting a compound of formula (III)

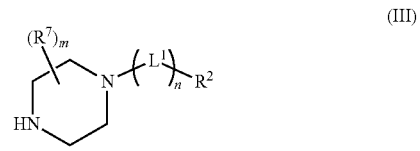

in which $L^1$, n, m, $R^2$ and $R^7$ are as defined by claim 1 with a compound of formula $R^9$—$(CH_2)_2$—$R^8$, in which $R^8$ and $R^9$, wherein $R^8$ and $R^9$, identical or different, represent a leaving group;

(ii) protecting an acid function of a compound of formula (II)

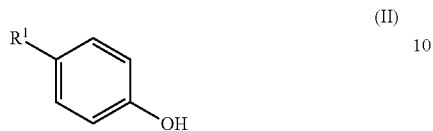

in which $R^1$ represents —$C(O)CR^3R^4CR^5R^6C(O)OH$; $R^3$, $R^4$, $CR^5$ and $R^6$ are as defined in claim 1;

(iii) reacting a compound obtained in step (i) with the compound obtained in step (ii); and (iv) deprotecting a compound obtained at step (iii).

12. A medication comprising the compound according to claim 1.

13. A method for treating insulin-resistance syndrome, the method comprising administering an effective quantity of the compound according to claim 1 to a patient in need thereof.

14. The method according to claim 13, wherein the insulin-resistance syndrome is type 2 diabetes.

15. A pharmaceutical composition comprising, as active principle, at least one compound according to claim 1.

16. The pharmaceutical composition according to claim 15, further comprising at least one other anti-diabetic agent.

* * * * *